(12) United States Patent
Dwivedi et al.

(10) Patent No.: US 8,759,518 B2
(45) Date of Patent: Jun. 24, 2014

(54) INTERMEDIATES FOR THE PREPARATION OF HMG COA REDUCTASE INHIBITORS AND PROCESSES FOR THE PREPARATION THEREOF

(75) Inventors: Shriprakash Dhar Dwivedi, Gujarat (IN); Dhimant Jasubhai Patel, Gujarat (IN); Mahesh Laljibhai Rupapara, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 8 days.

(21) Appl. No.: 13/576,296

(22) PCT Filed: Feb. 23, 2011

(86) PCT No.: PCT/IN2011/000108
§ 371 (c)(1),
(2), (4) Date: Oct. 19, 2012

(87) PCT Pub. No.: WO2011/104725
PCT Pub. Date: Sep. 1, 2011

(65) Prior Publication Data
US 2013/0158263 A1  Jun. 20, 2013

(30) Foreign Application Priority Data

Feb. 23, 2010 (IN) .......................... 481/MUM/2010
Jun. 17, 2010 (IN) .......................... 1820/MUM2010

(51) Int. Cl.
| C07D 239/02 | (2006.01) |
| C07D 405/12 | (2006.01) |
| C07D 239/42 | (2006.01) |
| C07D 405/06 | (2006.01) |
| C07D 257/04 | (2006.01) |

(52) U.S. Cl.
CPC ............ C07D 405/12 (2013.01); C07D 239/42 (2013.01); C07D 405/06 (2013.01); C07D 257/04 (2013.01)
USPC ... 544/297; 548/251; 548/304.4; 548/304.07; 548/483; 549/373

(58) Field of Classification Search
USPC ............ 544/297; 548/251, 304.4, 304.7, 483; 549/373
See application file for complete search history.

(56) References Cited

U.S. PATENT DOCUMENTS

| 8,476,432 B2 * | 7/2013 | Ju et al. .......................... 544/297 |
| 8,524,914 B2 * | 9/2013 | Lee et al. .................... 548/304.7 |
| 2012/0136151 A1 * | 5/2012 | Lee et al. ...................... 544/297 |

FOREIGN PATENT DOCUMENTS

| WO | WO 2008044243 A2 * | 4/2008 |
| WO | WO 2010140765 A2 * | 12/2010 |
| WO | WO 2012002741 A2 * | 1/2012 |

OTHER PUBLICATIONS

Y. Brinkman et al., 6 Organic Letters, 4335-4338 (2004).*

* cited by examiner

*Primary Examiner* — James O Wilson
*Assistant Examiner* — Alexander R Pagano
(74) *Attorney, Agent, or Firm* — Ladas & Parry LLP

(57) ABSTRACT

A compound of Formula (1), is disclosed wherein $P_1$ and $P_2$ are alcohol protecting groups or 1,3-diol protecting group, R is selected from:

wherein $R_4a$ is selected from alkyl, aryl, arylalkyl and cycloalkyl,
Rc is selected from H, alkyl, aryl, alkaoxy, haloalkyl, monohaloalkyloxy, and dihaloalkyloxy,
Rd is selected from alkyl, aryl, arylalkyl, $CF_3$, halo and $NO_2$ and X is selected from O, N—H, N-alkyl and S,
Ra and Rb are same or different and each represents hydrogen, an alkyl group of 1 to 12 carbon atoms, an aryl group of 6 to 12 carbon atoms, or an aralkyl group of 7 to 12 carbon atoms.

36 Claims, 2 Drawing Sheets

INTERMEDIATES FOR THE PREPARATION OF HMG COA REDUCTASE INHIBITORS AND PROCESSES FOR THE PREPARATION THEREOF

RELATED APPLICATION INFORMATION

This application is a 371 of International Application PCT/IN2011/000108 filed 23 Feb. 2011 entitled "INTERMEDIATES FOR THE PREPARATION OF HMG COA REDUCTASE INHIBITORS AND PROCESSES FOR THE PREPARATION THEREOF", which was published in the English language on 1 Sep. 2011, with International Publication Number WO 2011/104725 A2, and which claims priority from Indian Patent Applications No.: 481/MUM/2010 filed 23 Feb. 2010 and 1820/MUM/2010 filed 17 Jun. 2010, the contents of which are incorporated herein by reference.

FIELD OF THE INVENTION

The invention relates to a novel compounds of Formula (1), process for the preparation of chiral diol sulfones of general Formula (1), and to the use of such compounds as intermediates for the preparation of HMG-CoA reductase inhibitors, like rosuvastatin, atorvastatin, pitavastatin, and the like.

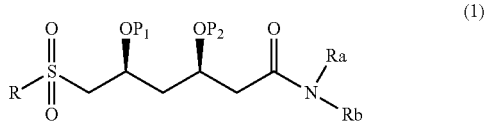

(1)

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

U.S. Pat. No. 6,875,867 B2 ("the '867 patent") discloses a process for the preparation of chiral diol sulfones of general Formula (1-A),

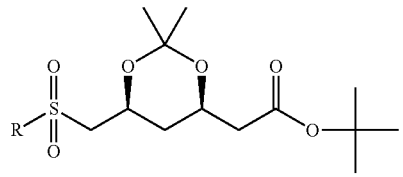

(1-A)

wherein R is as shown below:

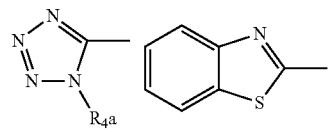

wherein $R_4a$ is preferably aryl such as phenyl.

U.S. Pat. No. '867 is directed to the synthesis of a chiral sulfone intermediate (prepared Kaneka alcohol preferably via triflate and sulfide intermediates) which is used in preparing a dihydroxy acid HMG CoA reductase inhibitor or lactone thereof. The invention also encompasses the process involving Juila-Kocienski olefination reaction wherein the chiral sulfone intermediate is reacted with a carboxylaldehyde to form the desired trans intermediate which may be converted to the final HMG CoA reductase inhibitor.

U.S. Pat. Nos. 6,344,569 and 5,278,313 disclose a process for the preparation 1,1-dimethylethyl(3R,5S)-6-chloro-3,5-dihydroxyhexanoate from (S)-4-chloro-3-hydroxybutyric acid ester (e.g. the specification of U.S. Pat. No. 1,723,728) as shown in scheme-1, which is the key intermediate for the synthesis of chiral diol sulfone of general Formula (1-A). U.S. Pat. No. 6,344,569 further discloses the process for the conversion of 1,1-dimethylethyl(3R,5S)-6-chloro-3,5-dihydroxyhexanoate to 1,1-dimethylethyl-(4R,6S)-6-chloromethyl-2,2-dimethyl-1,3-dioxane-4-acetate in example-3. Both the patents are provided herein as reference in its entirety.

Scheme-1

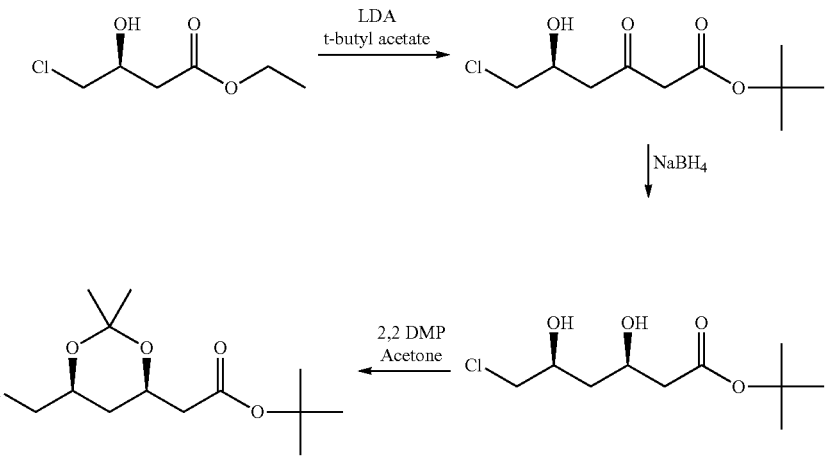

International (PCT) Publication WO 2008/644243 A2 provides a process for the preparation of statin derivatives or its pharmaceutically acceptable salts thereof of general Formula through novel intermediates,

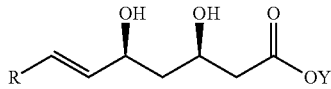

wherein '=' denotes single or double bond and Y is H, Na, K, Mg, Ca and R is as defined above from compounds of HMG-CoA reductase residues like a to i.

Particularly, for instance rosuvastatin calcium salt of Formula 9a is prepared by employing Julia-modified olefination,

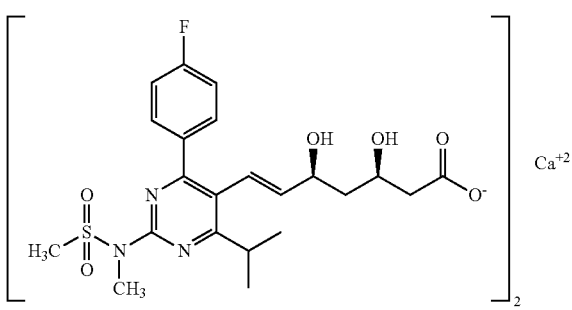
(9a)

which comprises of the following steps:
reacting the sulfone compound of Formula-2a

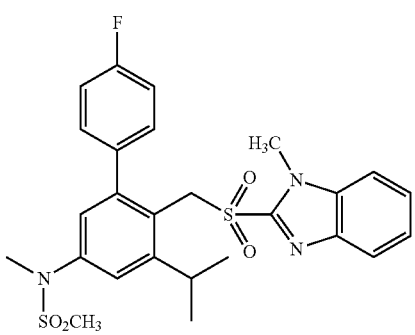
(2a)

with n-butyl amide compound of Formula-3b

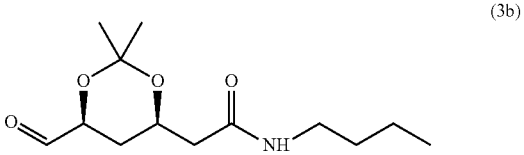 [SMILES: CCCCNC(=O)C[C@H]1C[C@@H](C=O)OC(C)(C)O1]
(3b)

in presence of a suitable alkali metal carbonate like potassium carbonate in a polar aprotic solvent like dimethyl sulfoxide, followed by isolation using cyclohexane to provide corresponding olefin compound of Formula-4a.

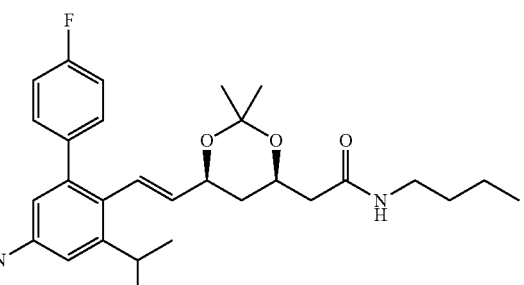
(4a)

The olefin compound of Formula-4a can be converted to dihydroxy compound of Formula-4x by deprotecting the acetonide protection with acid hydrolysis followed by preparation of tertiary butylamine salt of rosuvastatin of Formula-5a and finally converting the salt to rosuvastatin calcium of Formula-9a as shown in Scheme-2.

Scheme-2

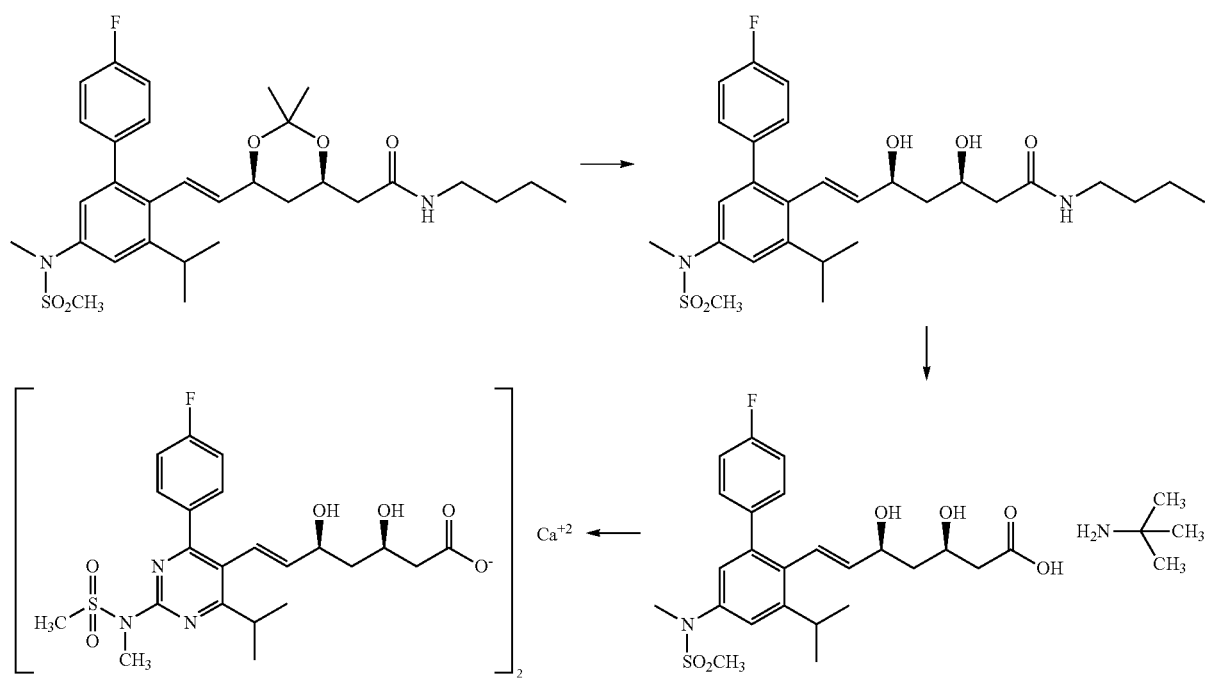

The similar process is employed for the preparation of other statin derivatives by changing the starting material via Julia-modified olefination process.

The process for the preparation of chiral diol sulfones of general Formula 1 as reported in the prior art involves two many steps starting from (S)-4-chloro-3-hydroxybutyric acid ester via kaneka alcohol. The process involves formation of triflate compound followed by condensation with thiol derivative to give thioether derivative. The S-oxidation of thioether derivative provides Julia Kocienski type intermediate.

International (PCT) Publications WO 2006/126035 A2, WO 2007/125547 A1 and WO 2010/023678 A1 discloses an alternative process for the preparation of rosuvastatin calcium.

U.S. Pat. No. 6,844,437 B1 and U.S. Pat. No. 6,784,171 B2 provides a process for the preparation of tert-butyl (E)-(6-{2-[4-(4-fluorophenyl)-6-isopropyl-2-[methyl(methylsulfonyl) amino]pyrimidin-5-yl]vinyl}-(4R,6S)-2,2-dimethyl[1,3]dioxan-4-yl)acetate which comprises reaction of diphenyl[4-(4-fluorophenyl)-6-isopropyl-2-[methyl)methylsulfonyl)-amino[pyrimid-in-5-ylmethyl]phosphine oxide with tert-butyl 2-[(4R,6S)-6-formyl-2,2-dimethyl-1,3-dioxan-4-yl] acetate in the presence of a strong base.

The present inventors have found that use of chiral diol sulfone intermediate of general Formula (1) provides the better alternative to prepare rosuvastatin calcium in high yield and purity. The present process avoids long multistep synthesis processes as disclosed in U.S. Pat. Nos. 6,844,437 B1; 6,784,171 B2; and 6,875,867 B2 and WO 2008/644243 A2.

The disadvantages of the prior art include multiple steps resulting in difficult preparations, the use of expensive reagents and reagents that are difficult to use on a commercial scale. This makes the process more difficult to perform, and time consuming and expensive technique for purification.

Accordingly, there is a need for an improved process for the preparation of HMG-CoA reductase inhibitors like rosuvastatin and intermediates thereof that eliminates the problems of the prior art on a commercial scale in a convenient and cost efficient manner.

SUMMARY OF THE INVENTION

The inventors of the present invention provides novel intermediates, which is useful, and cost effective alternative as the key intermediate for the preparation of statin derivatives. The inventors of the present invention have found novel process for preparation of HMG CoA reductase inhibitors by using novel intermediates of this invention.

According to first aspect, there is provided a novel compound of general Formula (1)

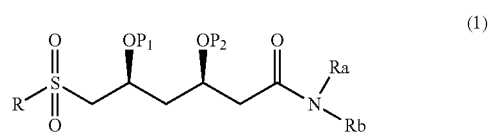

wherein $P_1$ and $P_2$ are alcohol protecting group or 1,3-diol protecting group and R is

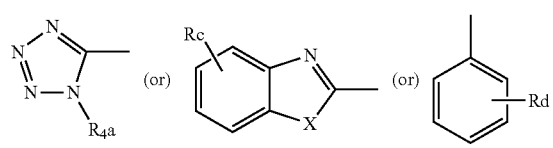

where $R_4a$ is alkyl, aryl, arylalkyl or cycloalkyl,
Rc is H, alkyl, aryl, alkaoxy, haloalkyl, monohaloalkyloxy, dihaloalkyloxy,
Rd is alkyl, aryl, arylalkyl, $CF_3$, halo or $NO_2$ and X is O, N—H, N-alkyl or S, Ra and Rb may be the same or different and each represents hydrogen, any of an alkyl group of 1 to 12 carbon atoms, an aryl group of 6 to 12 carbon atoms, an aralkyl group of 7 to 12 carbon atoms.

According to second aspect, there is provided a novel compound of general Formula (2)

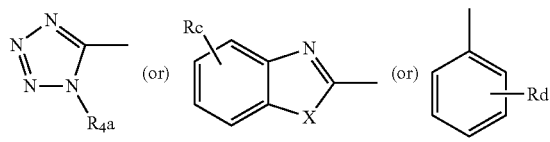
(2)

wherein $P_1$ and $P_2$ are alcohol protecting group or 1,3-diol protecting group and R is

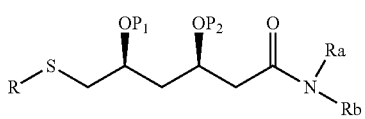

where $R_4a$ is alkyl, aryl, arylalkyl or cycloalkyl,

Rc is H, alkyl, aryl, alkaoxy, haloalkyl, monohaloalkyloxy, dihaloalkyloxy,

Rd is alkyl, aryl, arylalkyl, $CF_3$, halo or $NO_2$ and X is O, N—H, N-alkyl or S, Ra and Rb may be the same or different and each represents hydrogen, an alkyl group of 1 to 12 carbon atoms, an aryl group of 6 to 12 carbon atoms, an aralkyl group of 7 to 12 carbon atoms.

According to third aspect, there is provided a compound of Formula (5)

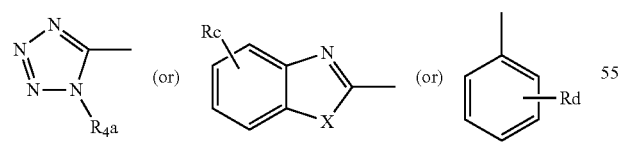
(5)

wherein R is

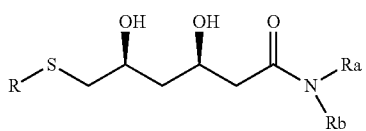

where $R_4a$ is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, $CF_3$, halo or $NO_2$ and X is O, N—H, N-alkyl or S, Ra and Rb may be the same or different and each represents hydrogen, any of an alkyl group of 1 to 12 carbon atoms, an aryl group of 6 to 12 carbon atoms, an aralkyl group of 7 to 12 carbon atoms.

According to fourth aspect, there is provided a compound of Formula (6)

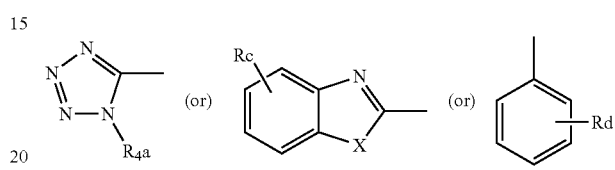
(6)

wherein R is

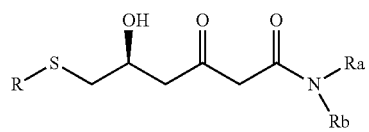

where $R_4a$ is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, $CF_3$, halo or $NO_2$ and X is O, N—H, N-alkyl or S; Ra and Rb may be the same or different and each represents hydrogen, any of an alkyl group of 1 to 12 carbon atoms, an aryl group of 6 to 12 carbon atoms, an aralkyl group of 7 to 12 carbon atoms.

According to an important aspect, there is provided novel compounds of Formula (8)

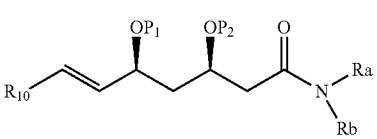
(8)

wherein $P_1$ and $P_2$ are alcohol protecting group or 1,3-diol protecting group, Ra and Rb may be the same or different and includes any of an alkyl group of 1 to 12 carbon atoms, an aryl group of 6 to 12 carbon atoms, an aralkyl group of 7 to 12 carbon atoms, $R_{10}$ is a hydrophobic anchor or residue of an HMG-CoA reductase inhibitor can be selected from compounds of Formula (a) to (i),

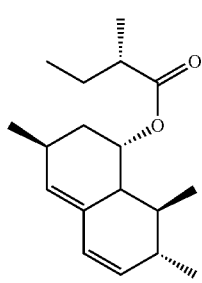
(a)

(b) 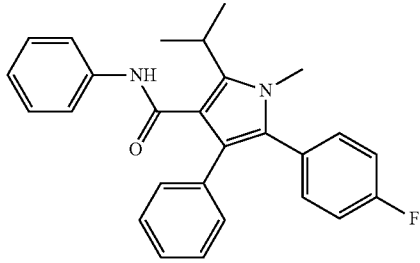

(c) 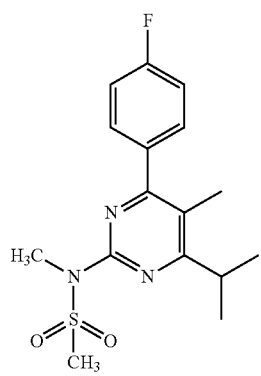

(d) 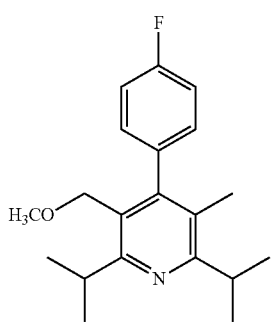

(e) 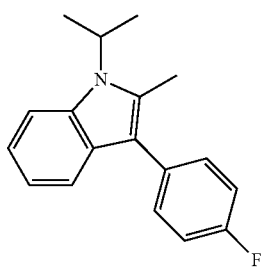

(f) 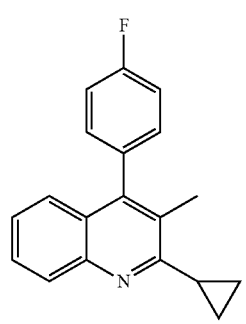

(g) 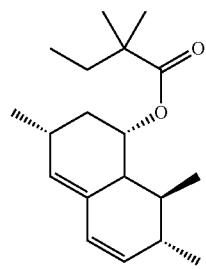

(h) 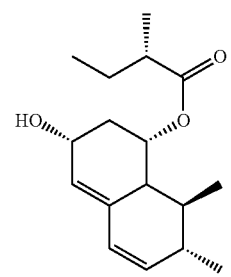

(i) 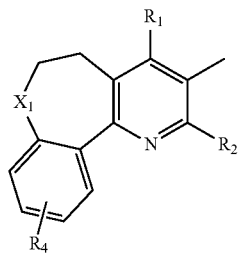

where $X_1$ is $CH_2$, O, S or $NR_7$, $R_1$ and $R_2$ are the same or different and are independently selected from alkyl, arylalkyl, cycloalkyl, alkenyl, cycloalkenyl, aryl, heteroaryl or cycloheteroalkyl, $R_4$ is H, halogen, $CF_3$, hydroxy, alkyl, alkoxy, alkanoylamino, aroylamino, or cyano, $R_7$ is H, alkyl, aryl, alkanoyl, aroyl, or alkoxycarbonyl.

According to further aspect, there is provided a compound of Formula (11)

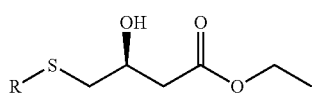
(11)

wherein R is

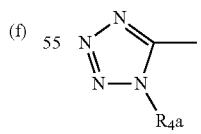 (or) 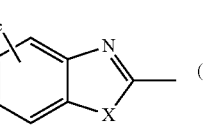 (or) 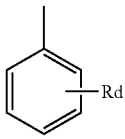

where $R_4a$ is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, $CF_3$, halo or $NO_2$ and X is O, N—H, N-alkyl or S.

Accordingly in one of the important aspect of the invention, there is provided a process for the preparation of compound of Formula (1)

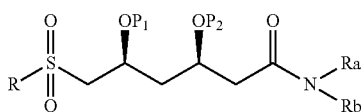 (1)

wherein $P_1$ and $P_2$ are alcohol protecting group or 1,3-diol protecting group and wherein R is

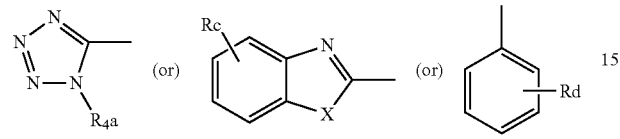

where $R_4a$ is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, $CF_3$, halo or $NO_2$ and X is O, N—H, N-alkyl or S, Ra and Rb may be the same or different and each represents hydrogen, any of an alkyl group of 1 to 12 carbon atoms, an aryl group of 6 to 12 carbon atoms, an aralkyl group of 7 to 12 carbon atoms, the process comprising:

(a) reacting (S)-4-chloro-3-hydroxybutyric acid ester (7)

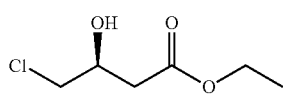 (7)

with thiol derivatives of Formula 3

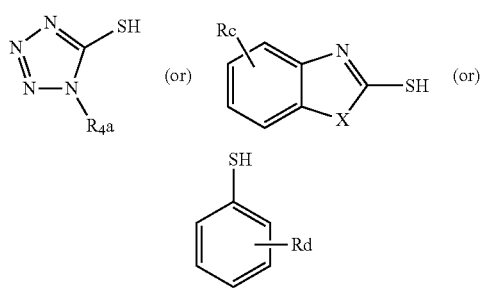 (3)

where $R_4a$, Rc, Rd and X are defined as above, in suitable organic solvent in presence of base to obtain compound of Formula (11)

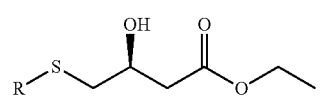 (11)

(b) reacting compound of Formula (11) with compound of Formula (7a)

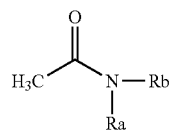 (7a)

Ra and Rb may be the same or different and each represents hydrogen, any of an alkyl group of 1 to 12 carbon atoms, an aryl group of 6 to 12 carbon atoms, an aralkyl group of 7 to 12 carbon atoms, in an inert organic solvent to obtain compound of Formula (6)

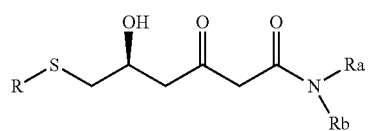 (6)

(c) treating compound of Formula (6) with dialkylalkoxyborane in presence of base to obtain compound of Formula (5);

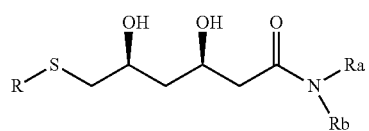 (5)

(d) reacting the compound of Formula (5) with suitable reagent in presence of catalyst in a polar organic solvent to obtain compound of Formula (2);

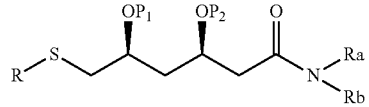 (2)

wherein R, $P_1$, $P_2$, Ra and Rb are as defined above;

(e) oxidizing the compound of Formula 2 with suitable oxidant to provide the compound of Formula 1.

According to further important aspect of the present invention, there is provided a process for the preparation of compound of Formula 8,

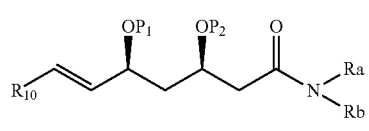 (8)

wherein $P_1$ and $P_2$ are alcohol protecting group or 1,3-diol protecting group, Ra and Rb may be the same or different and each represents any of an alkyl group of 1 to 12 carbon atoms, an aryl group of 6 to 12 carbon atoms, an aralkyl group of 7 to 12 carbon atoms, $R_{10}$ is a hydrophobic anchor or residue of an HMG-CoA reductase inhibitor can be selected from compounds of Formula (a) to (i),

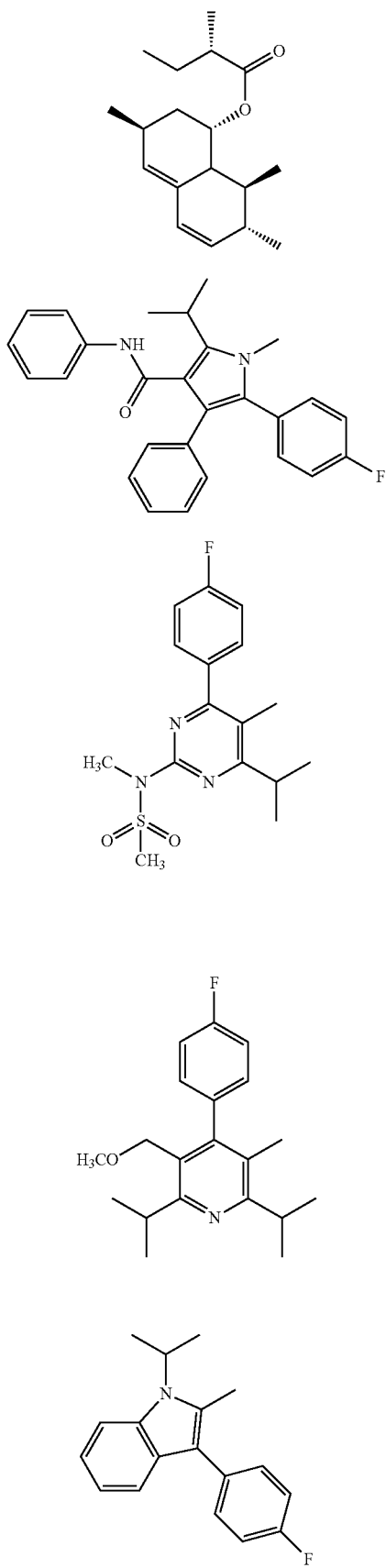

(a)
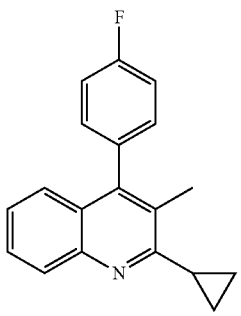

(f)

(b)

(g)
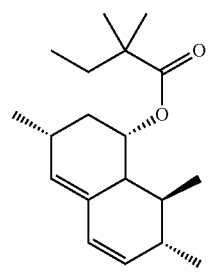

(c)

(h)
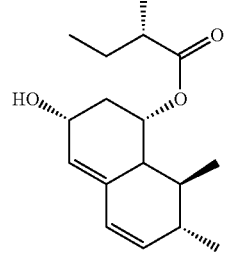

(d)

(i)
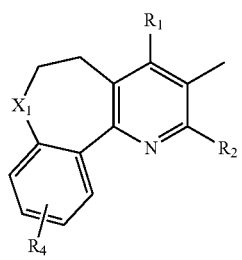

(e)

where $X_1$ is $CH_2$, O, S or $NR_7$, $R_1$ and $R_2$ are the same or different and are independently selected from alkyl, arylalkyl, cycloalkyl, alkenyl, cycloalkenyl, aryl, heteroaryl or cycloheteroalkyl, $R_4$ is H, halogen, $CF_3$, hydroxy, alkyl, alkoxy, alkanoylamino, aroylamino, or cyano, $R_7$ is H, alkyl, aryl, alkanoyl, aroyl, or alkoxycarbonyl, the process comprising: condensing a compound of Formula (1) with aldehyde compound of Formula

wherein $R_{10}$ is as defined above in presence of base such as sodium hydride, potassium tert-butoxide, LiHMDS or NaHMDS in an inert organic solvent to obtain of compound of Formula (8).

In one of the aspect of the invention, there is provide a process for the preparation of HMG-CoA reductase inhibitors of Formula (9)

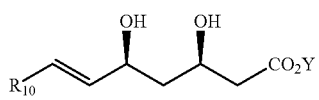

(9)

wherein Y is Na⁺, K⁺, Li⁺, Mg²⁺, Ca²⁺, Zn²⁺, Ba²⁺, Sr²⁺; amine and $R_{10}$ is a hydrophobic anchor or residue of an HMG-CoA reductase inhibitor and can be selected from compounds of Formula (a) to (i),

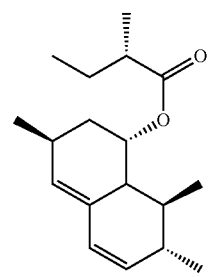

(a)

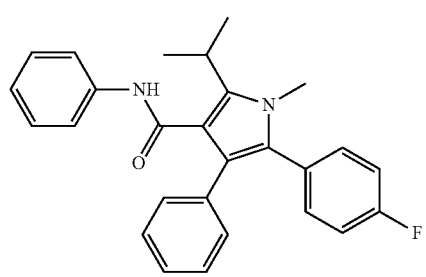

(b)

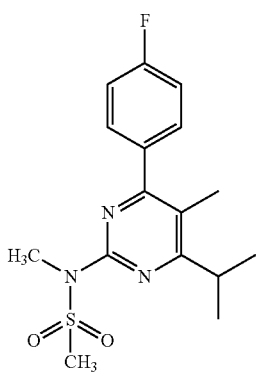

(c)

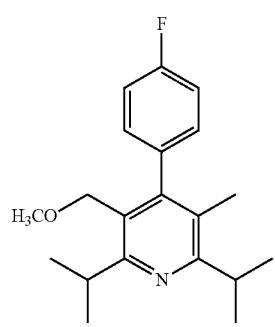

(d)

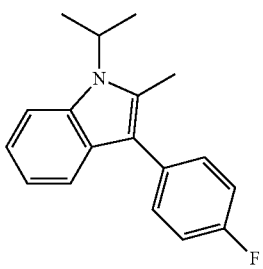

(e)

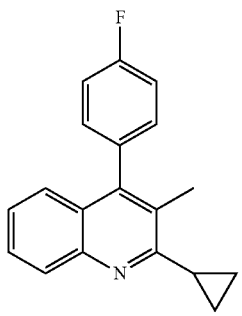

(f)

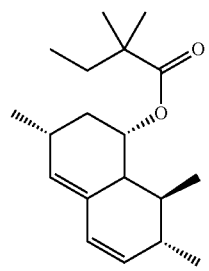

(g)

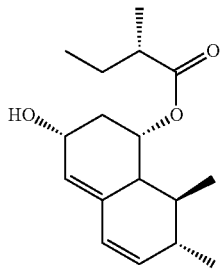

(h)

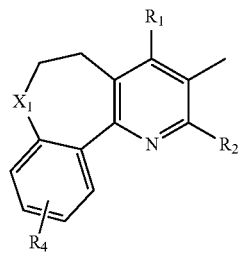

(i)

wherein $R_1$ and $R_2$ are same or different and are independently selected from alkyl, arylalkyl, cycloalkyl, alkenyl, cycloalkenyl, aryl, heteroaryl or cycloheteroalkyl; $R_4$ is H, halogen, $CF_3$, hydroxy, alkyl, alkoxy, alkanoylamino, aroylamino, or cyano; and $X_1$ is $CH_2$, O, S or $NR_7$, wherein $R_7$ is H, alkyl, aryl, alkanoyl, aroyl, or alkoxycarbonyl, the process comprising:

(a) condensing a compound of Formula (1)

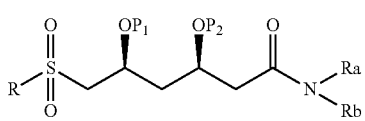

wherein $P_1$ and $P_2$ are alcohol protecting group or 1,3-diol protecting group and wherein R is

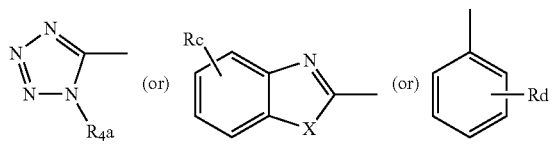

where $R_4a$ is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, $CF_3$, halo or $NO_2$ and X is O, N—H, N-alkyl or S, Ra and Rb may be the same or different and each represents, any of an alkyl group of 1 to 12 carbon atoms, an aryl group of 6 to 12 carbon atoms, an aralkyl group of 7 to 12 carbon atoms, with aldehyde compound

wherein $R_{10}$ is as defined above, in presence of base such as sodium hydride, potassium tert-butoxide, LiHMDS or NaHMDS in an inert organic solvent to obtain compound of Formula (8);

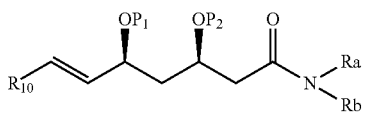

(b) hydrolyzing the compound of Formula (8) under acidic conditions to obtain compound of Formula (8A);

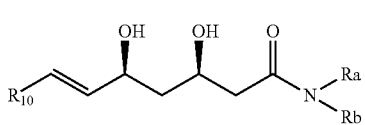

(c) treating the compound of Formula (8A) with an alkali metal hydroxide to form corresponding alkali metal salt of Formula (9)

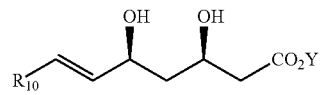

wherein, Y is $Na^+$, $K^+$, $Li^+$;

(d) optionally, treating alkali metal salt of HMG-CoA reductase inhibitors of Formula (9) with source of cation to obtain the HMG-CoA reductase inhibitors; and (e) isolating the HMG-CoA reductase inhibitors of Formula (9).

According to the still further embodiments, the parameters of the process may be altered by changing the 1,3-diol protecting group. Hence, it is also the scope of the present invention to provide compound of Formula (1a-A), (1a-C) and (1a-D) by the process disclosed herein above.

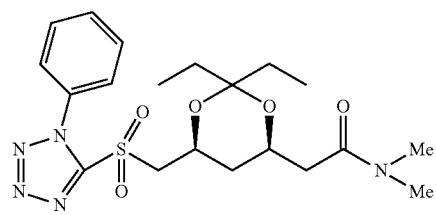

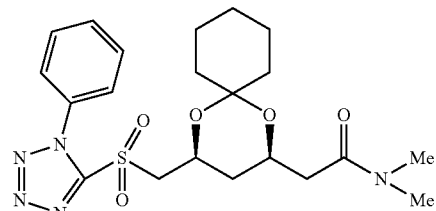

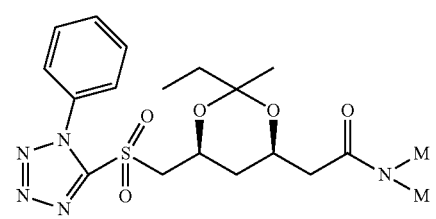

It will be within the scope of the present invention wherein the deprotecting the 1,3-diol protecting group of the product of Formula (8) can be hydrolyzed first with suitable acid and then removal of amide group by treatment with base with the provision both the hydrolysis sequence can be interchangeable to obtain compound of Formula (9), wherein $R_{10}$ is as defined above and Y is H or a pharmaceutically acceptable cation; and optionally followed by neutralization to give a compound of Formula (9) wherein Y is H, and/or optionally followed by conversion to another compound of Formula (9) wherein Y is calcium to obtain rosuvastatin calcium of Formula (9a).

Further process may include the further reacting alkali metal salt of compound of formula (9) with calcium acetate to obtain rosuvastatin calcium (9a).

In an important aspect of the present invention, there is provided a compound 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)-N,N-dimethylacetamide of Formula (8B2).

The compound of formula (8B2) is characterized by X-ray powder diffraction pattern and IR spectra as depicted in FIG. 1 and FIG. 2, respectively.

The details of one or more embodiments of the invention are set forth in the description below. Other features, objects and advantages of the invention will be apparent from the description and claims.

DETAILED DESCRIPTION OF THE INVENTION

Figure 1:
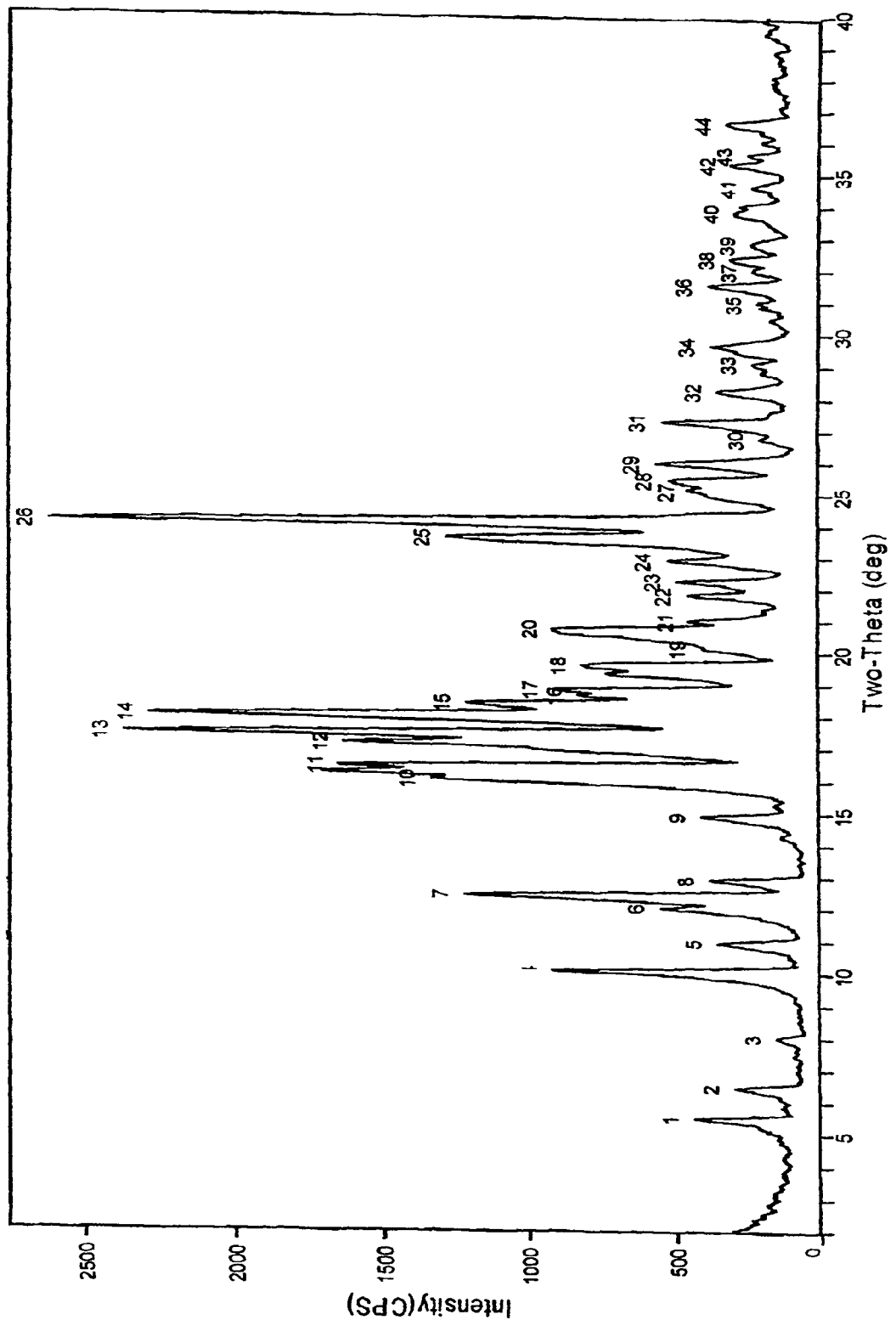
FIG. 1: X-ray powder diffraction of crystalline compound of formula (8B2).
Figure 2:
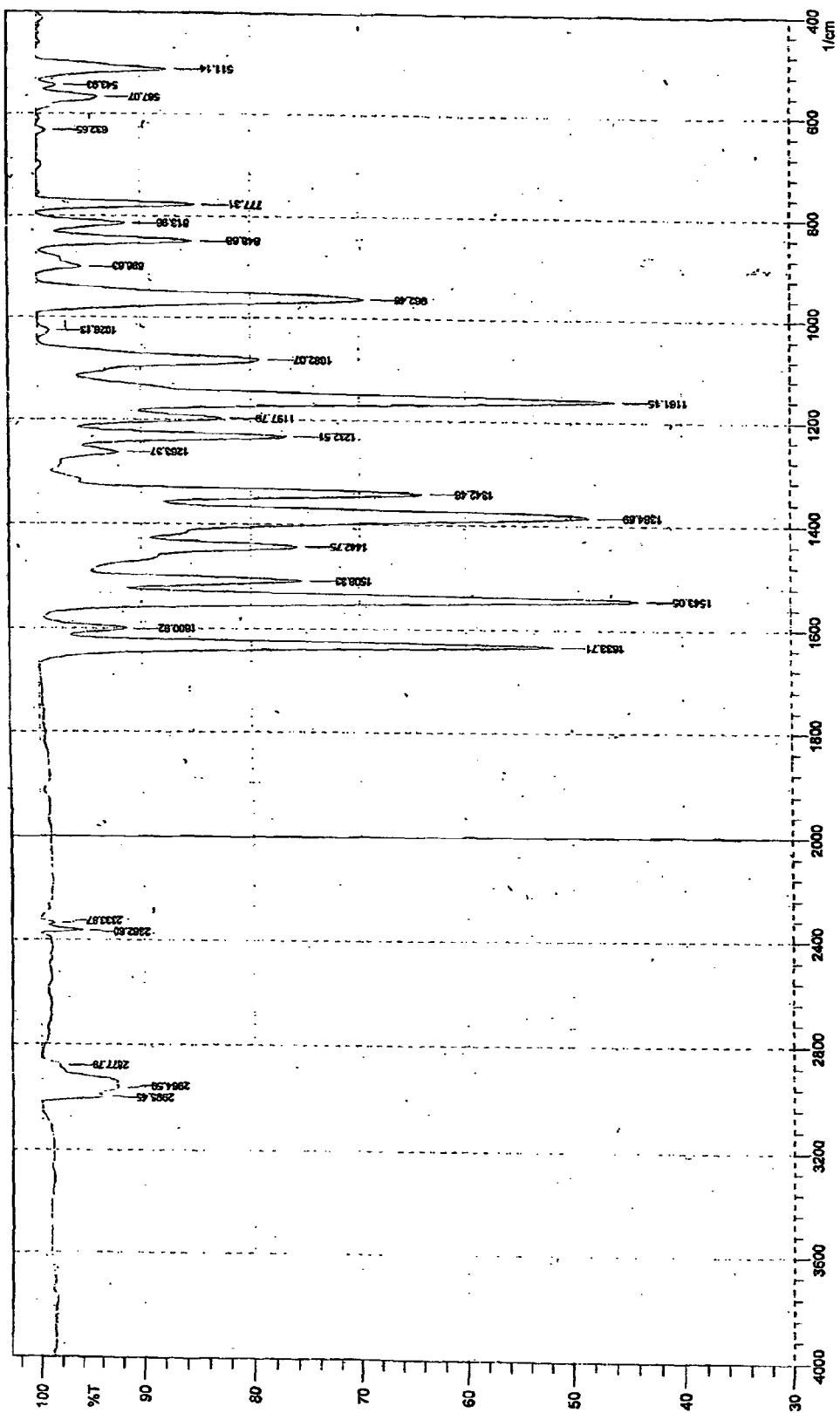
FIG. 2: IR spectra of crystalline compound of formula (8B2).

According to one embodiment, there is provided a novel compound of general Formula (1)

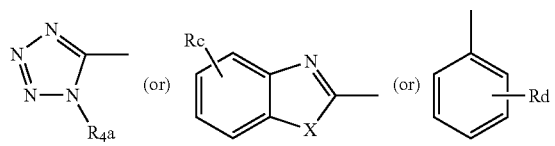
(1)

wherein $P_1$ and $P_2$ are alcohol protecting group or 1,3-diol protecting group and R is

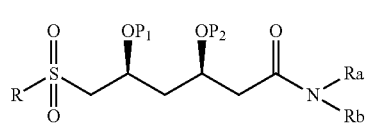

where $R_4a$ is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, $CF_3$, halo or $NO_2$ and X is O, N—H, N-alkyl or S, Ra and Rb may be the same or different and each represents hydrogen, any of an alkyl group of 1 to 12 carbon atoms, an aryl group of 6 to 12 carbon atoms, an aralkyl group of 7 to 12 carbon atoms.

In general, the $P_1$ and $P_2$ are alcohol protecting groups, or $P_1$ and $P_2$ taken together is a 1,3-diol protecting group selected from one or more of

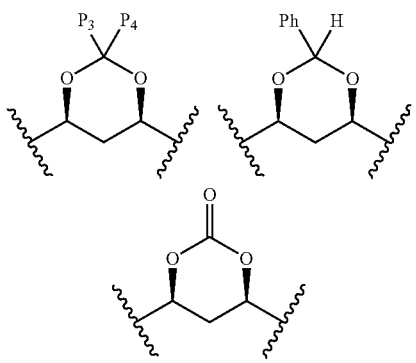

where $P_3$ and $P_4$ are independently (1-4C)alkyl or $P_3$ and $P_4$ taken together with the carbon atom to which they are attached, form a cyclopentyl, cyclohexyl or cycloheptyl ring.

According to the preferred embodiment, the compound of formula (1) includes, one or more of compounds (1a-A), (1a-B), (1a-C) and (1a-D) which is represented by (a)

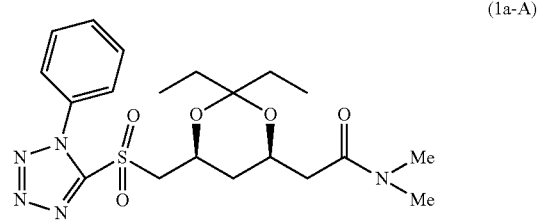
(1a-A)

(b)

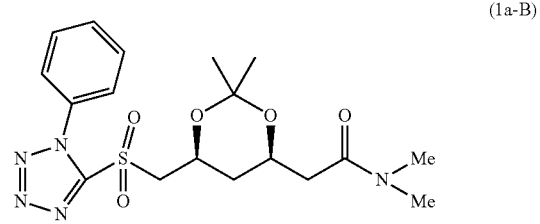
(1a-B)

(c)

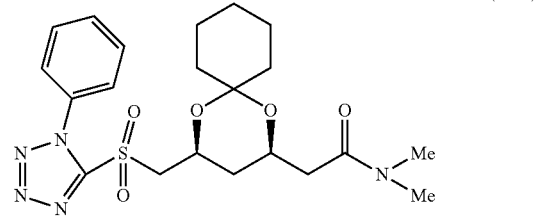
(1a-C)

(d)

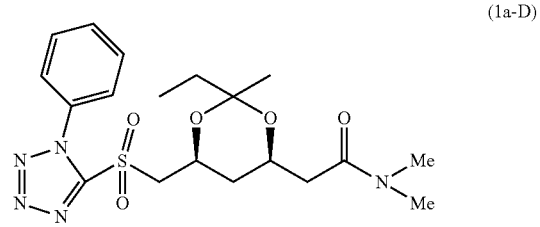
(1a-D)

According to another embodiment, there is provided a compound of general Formula (2),

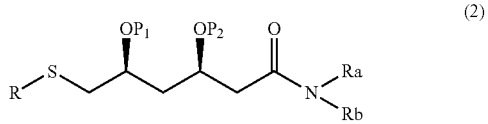
(2)

wherein $P_1$ and $P_2$ are alcohol protecting groups or 1,3-diol protecting group; R is:

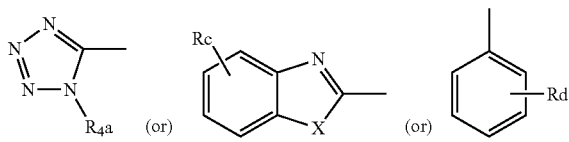

wherein $R_4a$ is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, $CF_3$, halo or $NO_2$ and X is O, N—H, N-alkyl or S, Ra and Rb may be same or different and each represents hydrogen, an alkyl group of 1 to 12 carbon atoms, an aryl group of 6 to 12 carbon atoms, or an aralkyl group of 7 to 12 carbon atom.

According to the preferred embodiment, the compound of formula (2) includes, one or more of compounds (2a-A), (2a-B), (2a-C) and (2a-D) which is represented by (a)

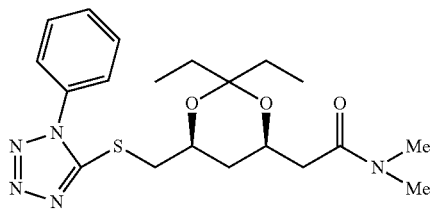

(2a-A)

(b)

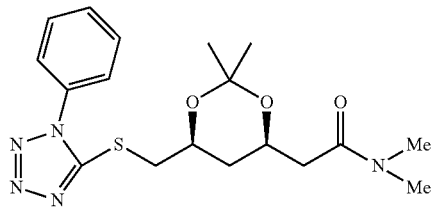

(2a-B)

(c)

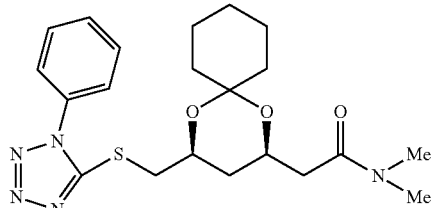

(2a-C)

(d)

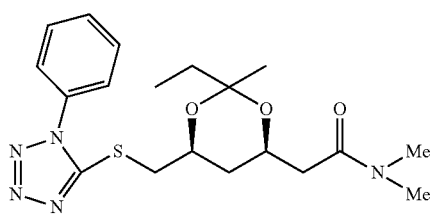

(2a-D)

According to another embodiment, there is provided a compound of Formula (5)

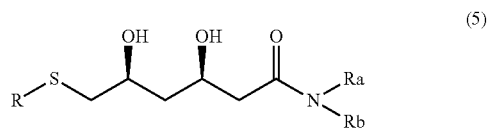

(5)

wherein R is

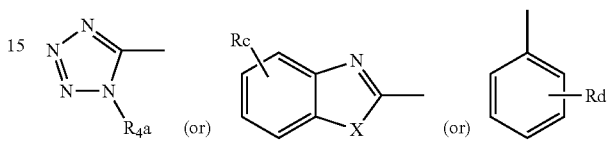

where $R_4a$ is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, $CF_3$, halo or $NO_2$ and X is O, N—H, N-alkyl or S, Ra and Rb may be the same or different and each represents hydrogen, any of an alkyl group of 1 to 12 carbon atoms, an aryl group of 6 to 12 carbon atoms, an aralkyl group of 7 to 12 carbon atoms.

In preferred aspect, the compound of formula (5) is represented by compound of formula (5a)

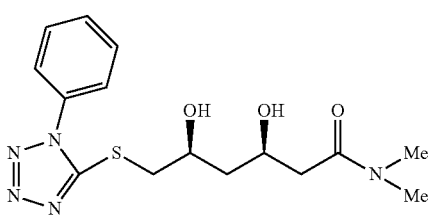

(5a)

According to still another embodiment, there is provided a compound of Formula (6)

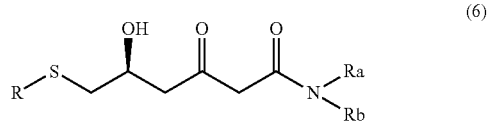

(6)

wherein R is

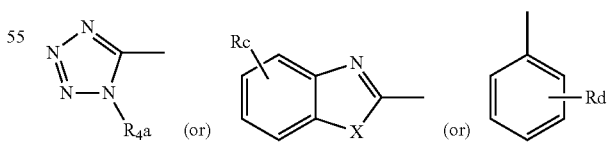

where $R_4a$ is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, $CF_3$, halo or $NO_2$ and X is O, N—H, N-alkyl or S; Ra and Rb may be the same or different and each represents hydrogen, any of an alkyl group of 1 to 12 carbon atoms, an aryl group of 6 to 12 carbon atoms, an aralkyl group of 7 to 12 carbon atoms.

According to further embodiment, there is provided a compound of Formula (8)

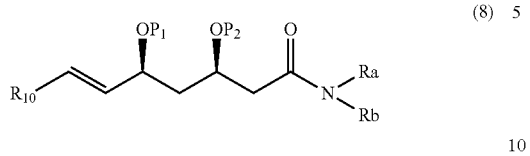
(8)

wherein $P_1$ and $P_2$ are alcohol protecting group or 1,3-diol protecting group, Ra and Rb may be the same or different and includes any of an alkyl group of 1 to 12 carbon atoms, an aryl group of 6 to 12 carbon atoms, an aralkyl group of 7 to 12 carbon atoms, $R_{10}$ is a hydrophobic anchor or residue of an HMG-CoA reductase inhibitor can be selected from compounds of Formula (a) to (i),

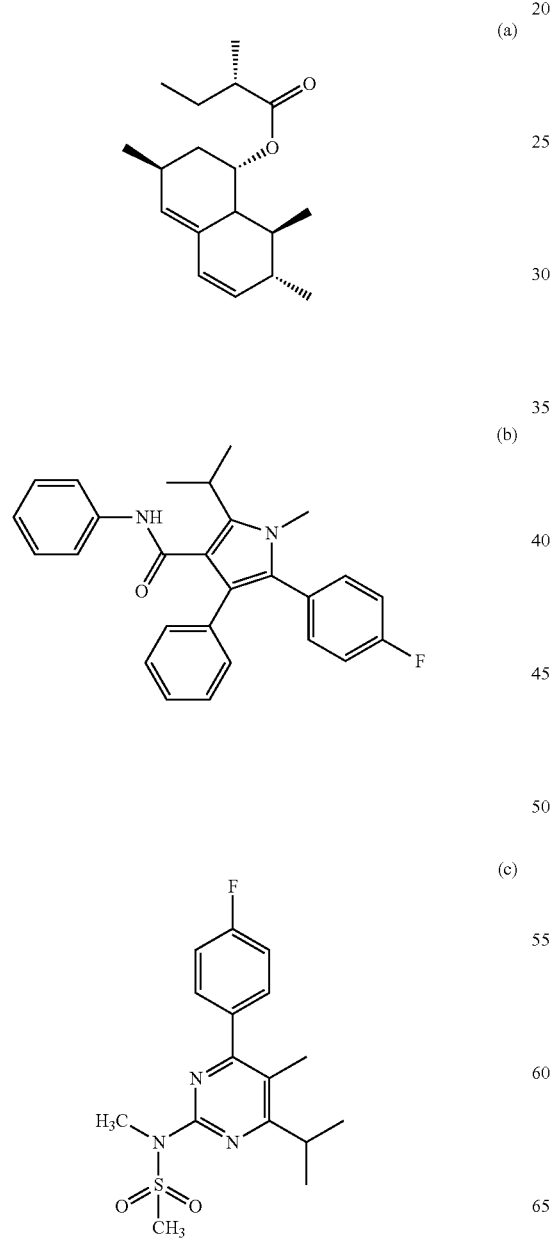

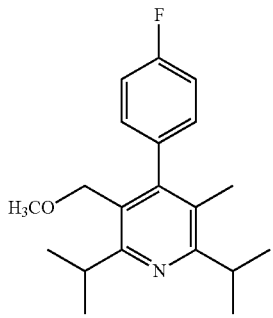
(d)

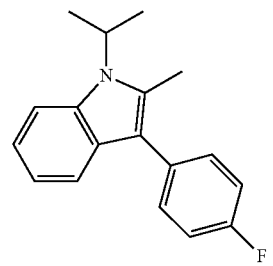
(e)

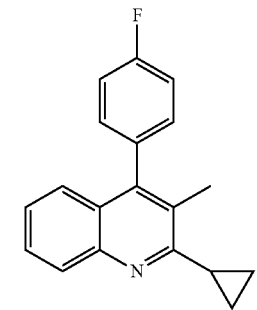
(f)

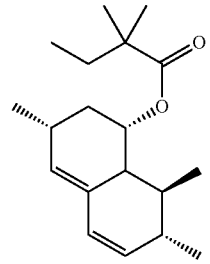
(g)

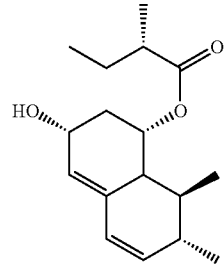
(h)

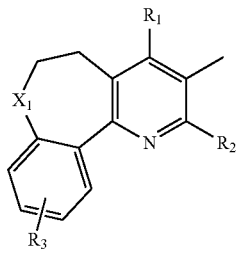

(i)

where $X_1$ is $CH_2$, O, S or $NR_7$, $R_1$ and $R_2$ are the same or different and are independently selected from alkyl, arylalkyl, cycloalkyl, alkenyl, cycloalkenyl, aryl, heteroaryl or cyclo-heteroalkyl, $R_4$ is H, halogen, $CF_3$, hydroxy, alkyl, alkoxy, alkanoylamino, aroylamino, or cyano, $R_7$ is H, alkyl, aryl, alkanoyl, aroyl, or alkoxycarbonyl.

According to the preferred embodiment, there is provided a compound of general Formula (8B),

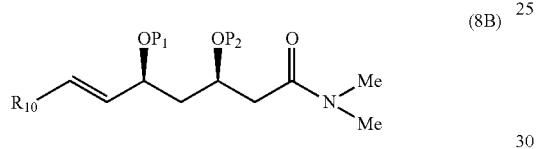

(8B)

wherein $P_1$ and $P_2$ are alcohol protecting groups or 1,3-diol protecting group;

$R_{10}$ is a hydrophobic anchor or a residue of an HMG-CoA reductase inhibitor and can be selected from compounds of Formula (a) to (i),

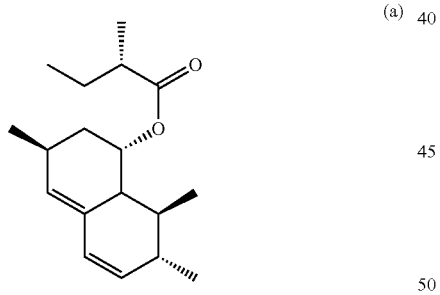

(a)

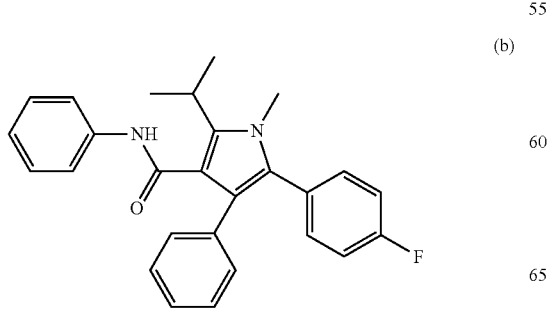

(b)

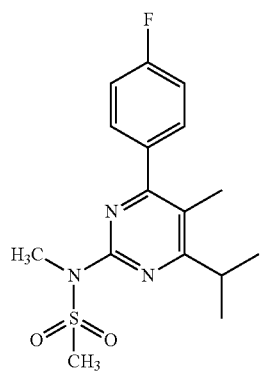

(c)

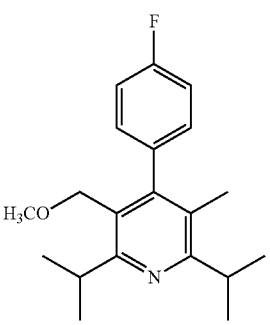

(d)

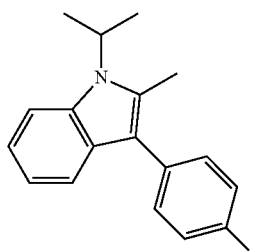

(e)

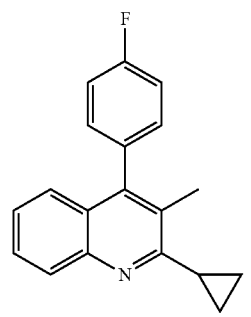

(f)

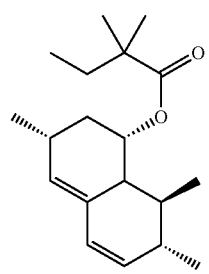

(g)

-continued (h) 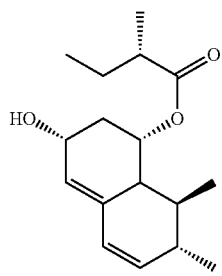

(i) 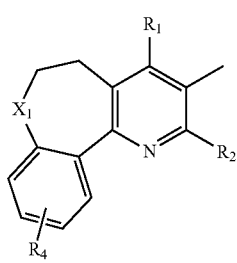

wherein $R_1$ and $R_2$ are same or different and are independently selected from alkyl, arylalkyl, cycloalkyl, alkenyl, cycloalkenyl, aryl, heteroaryl or cycloheteroalkyl, $R_4$ is H, halogen, $CF_3$, hydroxy, alkyl, alkoxy, alkanoylamino, aroylamino, or cyano, $X_1$ is $CH_2$, O, S or $NR_7$, wherein $R_7$ is H, alkyl, aryl, alkanoyl, aroyl, or alkoxycarbonyl.

According to the preferred embodiment, the compound of formula (8) includes, one or more of compounds (8B1), (8B2), (8B3) and (8B4) which is represented by (a) (8B1)

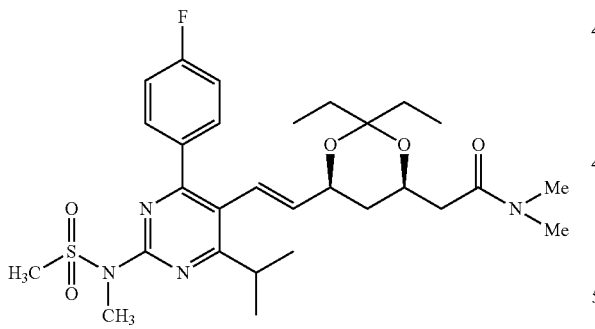

(b) (8B2)

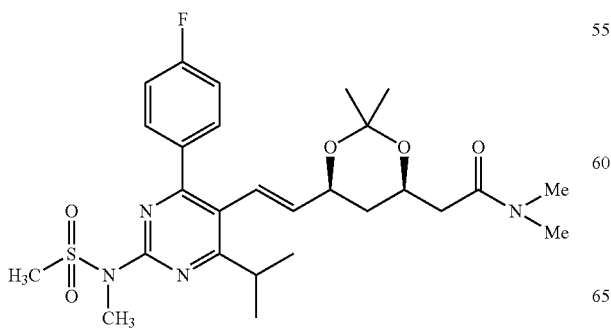

(c) (8B3)

(d) (8B4)

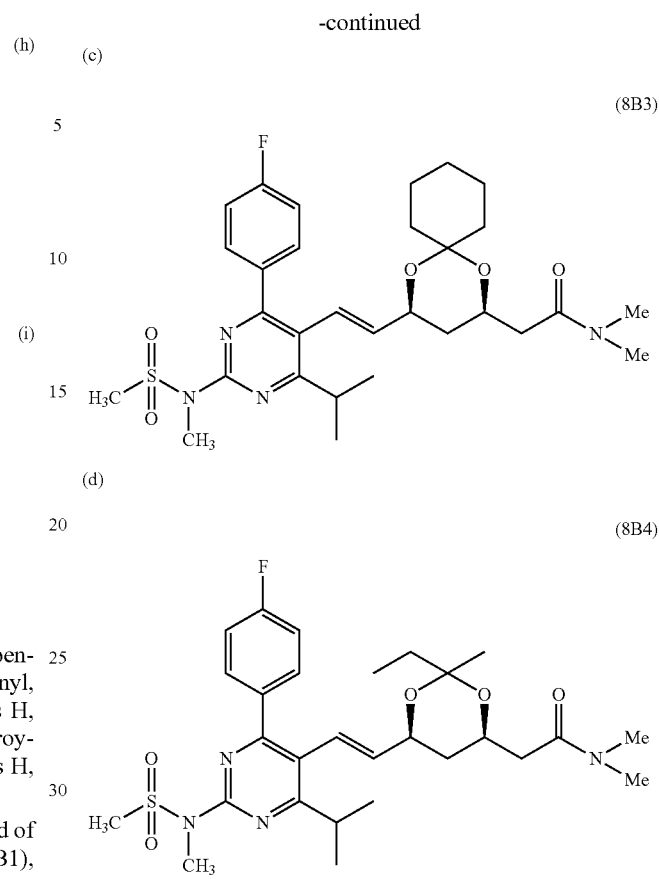

According to the preferred embodiment, there is provided a compound of Formula (11)

(11)

(a) 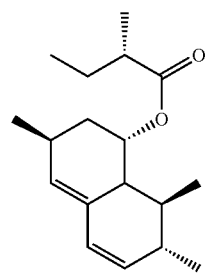

(b) 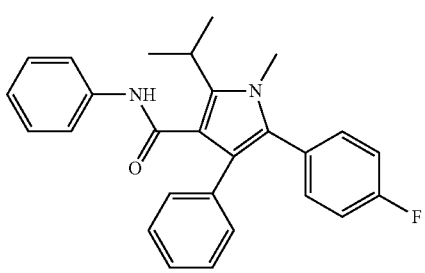

-continued (c)
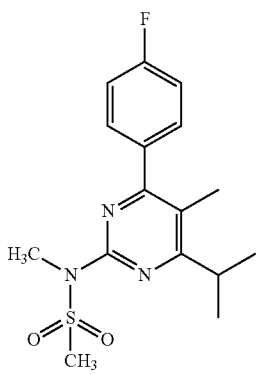

(d)
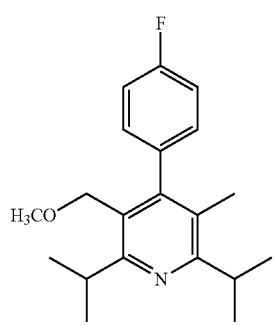

wherein R is

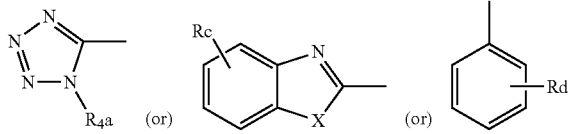

where R$_4$a is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, CF$_3$, halo or NO$_2$ and X is O, N—H, N-alkyl or S.

In further embodiment, the present invention provides a process for the preparation of compound of Formula (1)

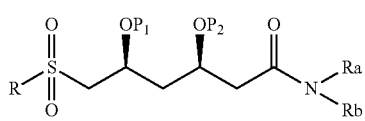 (1)

wherein P$_1$ and P$_2$ are alcohol protecting group or 1,3-diol protecting group and wherein R is

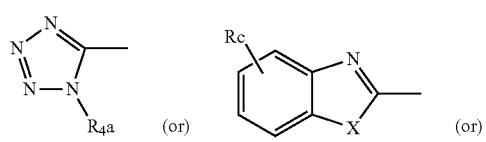

-continued

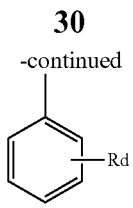

where R$_4$a is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, CF$_3$, halo or NO$_2$ and X is O, N—H, N-alkyl or S, Ra and Rb may be the same or different and each represents hydrogen, any of an alkyl group of 1 to 12 carbon atoms, an aryl group of 6 to 12 carbon atoms, an aralkyl group of 7 to 12 carbon atoms, the process comprising:

(a) reacting (S)-4-chloro-3-hydroxybutyric acid ester (7)

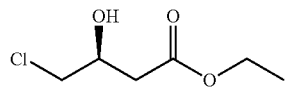 (7)

with thiol derivatives of Formula 3

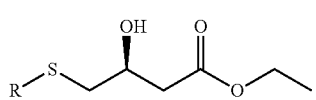 (3)

where R$_4$a, Rc, Rd and X are defined as above,
in suitable organic solvent in presence of base to obtain compound of Formula (11);

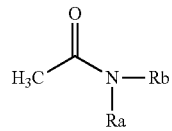 (11)

(b) reacting compound of Formula (11) with compound of Formula (7a)

(7a)

Ra and Rb may be the same or different and each represents hydrogen, any of an alkyl group of 1 to 12 carbon atoms, an aryl group of 6 to 12 carbon atoms, an aralkyl group of 7 to 12 carbon atoms, in an inert organic solvent to obtain sulfide derivative of Formula (6);

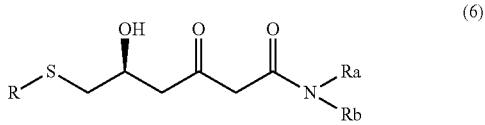

(6)

(c) treating compound (6) with dialkylalkoxyborane in presence of base to obtain compound of Formula (5);

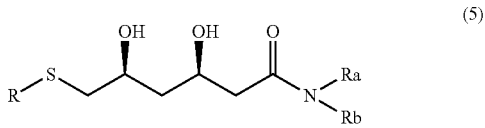

(5)

(d) reacting the compound of Formula (5) with suitable reagent in presence of catalyst in a polar organic solvent to obtain compound of Formula (2);

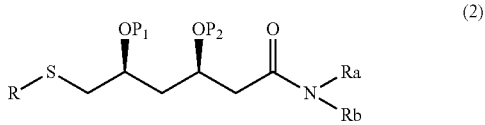

(2)

wherein R, $P_1$, $P_2$, Ra and Rb are as defined above;
(e) oxidizing the compound of Formula 2 with suitable oxidant to provide the compound of Formula 1.

Embodiments of the process includes preparation of the compounds of general Formula (1) from (S)-4-chloro-3-hydroxybutyric acid ester of Formula (7) by reacting with thiol derivatives of Formula (3),

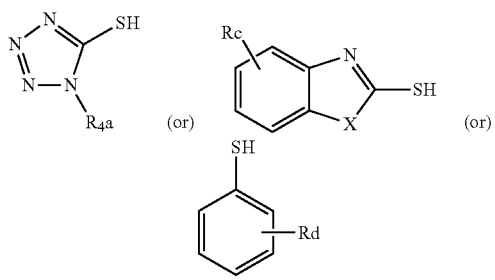

(3)

where $R_4a$ is alkyl, aryl, arylalkyl or cycloalkyl,
Rc is H, alkyl, aryl, alkaoxy, haloalkyl, monohaloalkyloxy, dihaloalkyloxy,
Rd is alkyl, aryl, arylalkyl, $CF_3$, halo or $NO_2$ and X is O, N—H, N-alkyl or S,
in suitable organic solvent from one or more of toluene, xylene, ethylbenzene, cyclohexane, hexane, heptane, methylene dichloride, ethylene dichloride, ethyl acetate and the like. In particular, the suitable organic solvent is toluene.

The reaction is performed in presence of base selected from one or more of inorganic base like sodium hydroxide, potassium hydroxide, sodium bicarbonate, potassium bicarbonate, sodium hydride, and the like or organic base like triethylamine, diisopropylethylamine, diisopropyl amine, DBU, pyridine and the like. In particular, the base is triethylamine.

The reaction can be performed at elevated temperature at about 50° C. to 120° C. In particular at about 80° C. to 85° C. The product after the reaction is completed is quenched with water to separate the layers. The separated organic layer is treated with HCl solution followed by water. The compound of general Formula (11) is isolated by removal of organic solvent.

In general, the further embodiments includes reacting compound of Formula (11) with amide compound of Formula (7a) in presence of lithium amide, preferably lithium diethylamide. The reaction is performed not below −50° C., preferably at about −45° C. in an inert organic solvent. The inert organic solvent as in step (b) can be selected from one or more of diethyl ether, THF, 2-methyl THF and the like. In particular, the solvent is THF.

The embodiments of the process includes reaction of compound (6) with dialkylalkoxyborane selected from one or more of diethylmethoxyborane, diethylethoxyborane, dimethylethoxyborane and the like. In particular, dialkylalkoxyborane is diethylmethoxybrane (DEMBO). The reaction is performed in the presence of base selected from one or more of alkali metal hydride like NaH, KH, LiH, NaBH4, KBH4, LiAlH4 and the like. In particular, the alkali metal hydride is sodium borohydride.

The reaction is preferably performed in the range of about −110° C. to −50° C. In particular from about −90° C. to about −70° C. in suitable organic solvent selected from one or more of 1,4-dioxane, THF, 2-methyl THF, diisopropyl ether, diethyl ether, methyl tertbutyl ether and the like. In particular, it is THF.

The embodiments of the process further includes purifying the compound of formula (5). The purification can be performed in one or more of organic solvents selected from $C_1$-$C_4$ alcohol, water, aliphatic hydrocarbons like n-hexane, n-heptane, cyclohexane, methylene dichloride, toluene and the like. In particular, the solvent is mixture of methanol and water followed by treatment with n-hexane and finally extraction with methylene dichloride.

The compound of Formula (5) is treated with suitable reagent for protecting 3,5-dihydroxy group in presence of catalyst one or more of camphor sulfonic acid, methane sulphonic acid, ethane sulfonic acid, pyridinium p-toluene sulfonic acid, p-toluene sulfonic acid and the like. In particular, the catalyst is methane sulfonic acid.

The embodiments includes the reacting the compound of formula (5) with suitable reagent like one or more of 2,2-dimethoxypropane, 2,2-dimethoxypentane, 1,1-dimethoxycyclohexane or 2,2-dimethoxybutane and the like to obtain compound of formula (2).

The suitable polar solvent is one or more of $C_1$-$C_4$ alcohol like methanol, ethanol, isopropanol, butanol and the like, $C_2$-$C_4$ ketone like acetone, methyl isobutyl ketone, amides like dimethyl formamide, nitriles like acetonitrile and the like. In particular, the polar solvent is acetone to obtain compound of Formula (2).

According to the preferred embodiments, the compound of formula (2) is oxidized with suitable oxidant selected from hydrogen peroxide, m-chloroperbenzoic acid, sodium hypochloride, N-chlorosuccimide, N-bromosuccinimide, oxone and the like. In particular, the oxidizing agent is hydrogen peroxide. The oxidation can be done in presence of an appropriate catalyst like ammonium heptamolybdate tetrahydrate, vanadium complexes like vanadium acetoacetonate and the like. In particular, the catalyst is ammonium heptamolybdate tetrahydrate.

In general, the oxidation of sulfide (2) is performed at about −10° C. to 40° C., particularly at about 0° C. to 5° C. to obtain compound of general Formula (1).

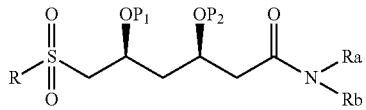

(1)

The compound of general formula (1) exists in the form of chiral sulfone diols but not limited to the chiral compounds only. The racemic compound is also considered to be the scope of the invention.

According to another preferred embodiment, there is provided a process for the preparation of compound of Formula 8,

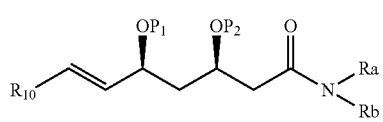

(8)

wherein $P_1$ and $P_2$ are alcohol protecting group or 1,3-diol protecting group, Ra and Rb may be the same or different and each represents any of an alkyl group of 1 to 12 carbon atoms, an aryl group of 6 to 12 carbon atoms, an aralkyl group of 7 to 12 carbon atoms, $R_{10}$ is a hydrophobic anchor or residue of an HMG-CoA reductase inhibitor can be selected from compounds of Formula (a) to (i),

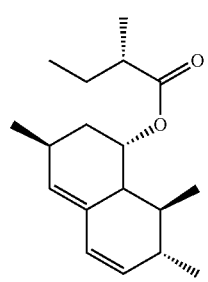

(a)

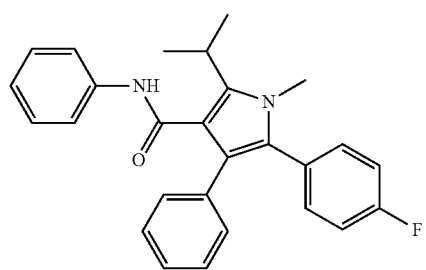

(b)

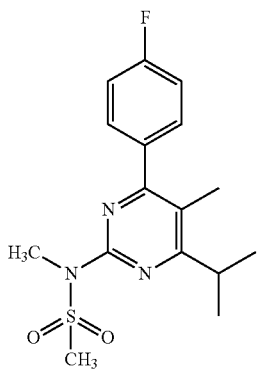

(c)

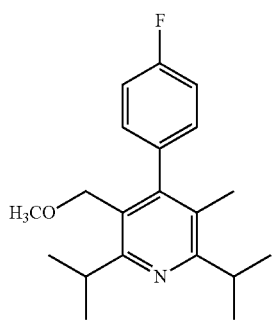

(d)

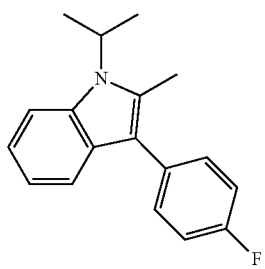

(e)

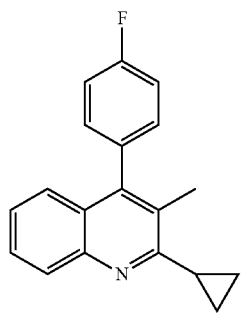

(f)

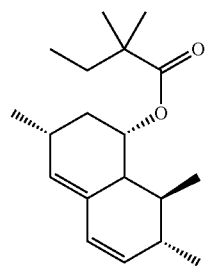

(g)

-continued (h)

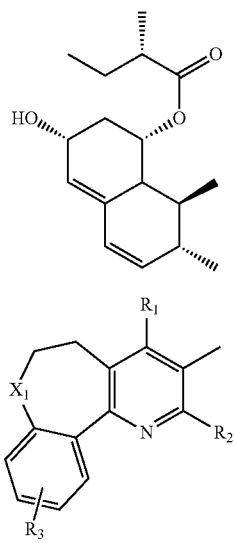

(i)

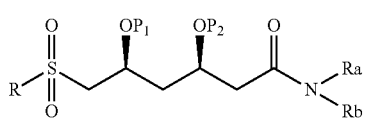

where $X_1$ is $CH_2$, O, S or $NR_7$; $R_1$ and $R_2$ are the same or different and are independently selected from alkyl, arylalkyl, cycloalkyl, alkenyl, cycloalkenyl, aryl, heteroaryl or cyclo-heteroalkyl, $R_4$ is H, halogen, $CF_3$, hydroxy, alkyl, alkoxy, alkanoylamino, aroylamino, or cyano, $R_7$ is H, alkyl, aryl, alkanoyl, aroyl, or alkoxycarbonyl. the process comprising: condensing a compound of Formula (1)

(1)

with aldehyde compound of Formula $$R_{10}-\overset{O}{\underset{}{\text{CH}}}$$

wherein $R_{10}$ is as defined above in presence of base such as sodium hydride, potassium tert-butoxide, LiHMDS or NaH-MDS in an inert organic solvent to obtain of compound of Formula (8).

In general, the organic solvent can be one or more of $C_1$-$C_4$ alcohol like methanol, ethanol, isopropanol, butanol and the like, $C_2$-$C_4$ ketone like acetone, methyl isobutyl ketone, amides like dimethyl formamide, dimethyl acetamide, N-methyl pyrrolidone, dimethylsulfoxide and the like. In particular, the organic solvent is dimethylsulfoxide.

The compound of Formula (8), prepared as per the process of the present invention is converted to HMG-CoA reductase inhibitors of Formula (9)

(9)

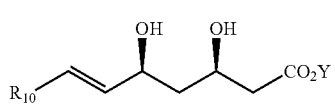

According to another embodiment, there is provided a process for the preparation of compound of Formula (8B2), (8B2)

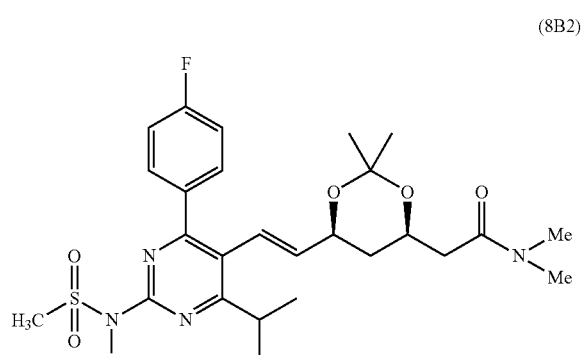

the process comprising:
(a) reacting compound of Formula (5a)

(5a)

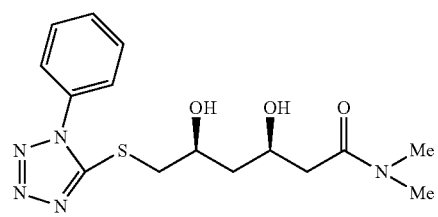

with 2,2-dimethoxypropane to obtain compound of Formula (2a-B)

(2a-B)

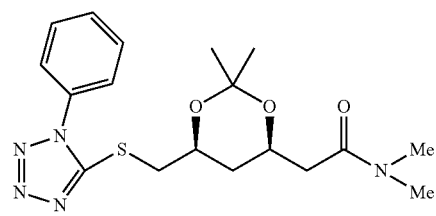

(b) oxidizing the compound of formula (2a-B) with suitable oxidant to provide a compound of the Formula (1a-B);

(1a-B)

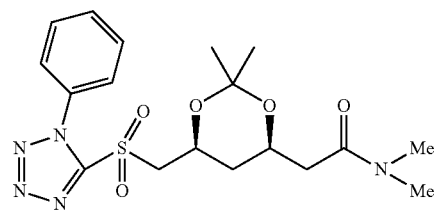

(c) condensing the compound of Formula (1a-B) with aldehyde compound of Formula

(5)

wherein $R_{10}$ is

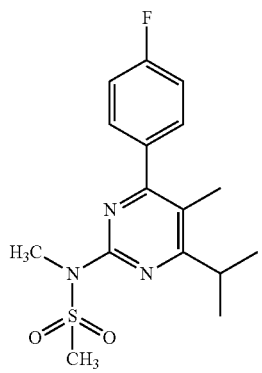

in presence of base such as sodium hydride, potassium tert-butoxide, LiHMDS or NaHMDS in a suitable organic solvent to obtain compound of Formula (8B2).

The embodiments of the process includes reaction of step (a) in presence of catalyst selected from one or more of camphor sulfonic acid, methane sulphonic acid, ethane sulfonic acid, pyridinium p-toluene sulfonic acid, p-toluene sulfonic acid and the like to obtain compound of formula (2a-B).

The process further involves oxidation of compound (2a-B) with suitable oxidant selected from one or more of hydrogen peroxide, m-chloroperbenzoic acid, sodium hypochloride, N-chlorosuccimide, N-bromosuccinimide, oxone and the like to obtain the compound of formula (1a-B).

Further embodiments includes condensation of compound (1a-B) with aldehyde compound as in step (c). The condensation is performed in presence of base such as sodium hydride, potassium tert-butoxide, LiHMDS or NaHMDS in a suitable organic solvent selected from one or more of $C_1$-$C_4$ alcohol like methanol, ethanol, isopropanol, butanol and the like, $C_2$-$C_4$ ketone like acetone, methyl isobutyl ketone, amides like dimethyl formamide, dimethyl acetamide, N-methyl pyrrolidone, dimethylsulfoxide and the like to obtain compound of formula (8B2). The compound of formula (8B2) can be isolated by any of the known techniques reported in the art.

According to the still further embodiments of the present invention, there is provided a process for the preparation of HMG-CoA reductase inhibitors of Formula (9)

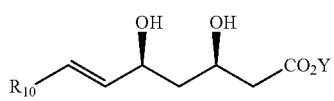
(9)

Y is $Na^+$, $K^+$, $Li^+$, $Mg^{2+}$, $Ca^{2+}$, $Zn^{2+}$, $Ba^{2+}$, $Sr^{2+}$; amine and $R_{10}$ is a hydrophobic anchor or residue of an HMG-CoA reductase inhibitor and can be selected from compounds of Formula (a) to (i)

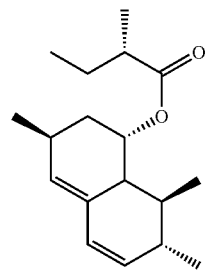
(a)

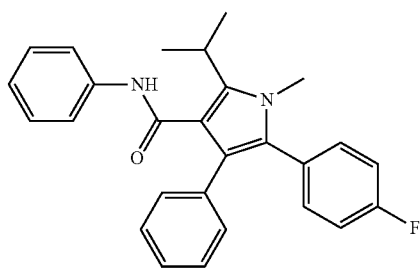
(b)

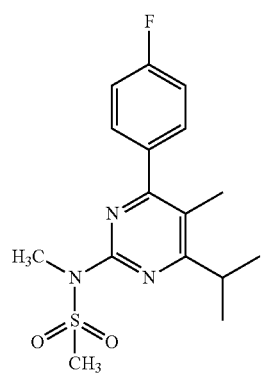
(c)

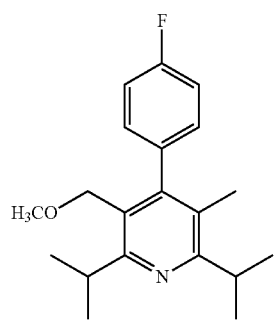
(d)

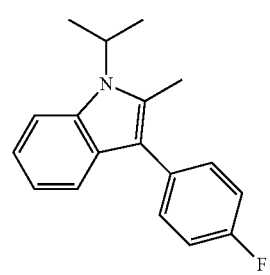
(e)

-continued

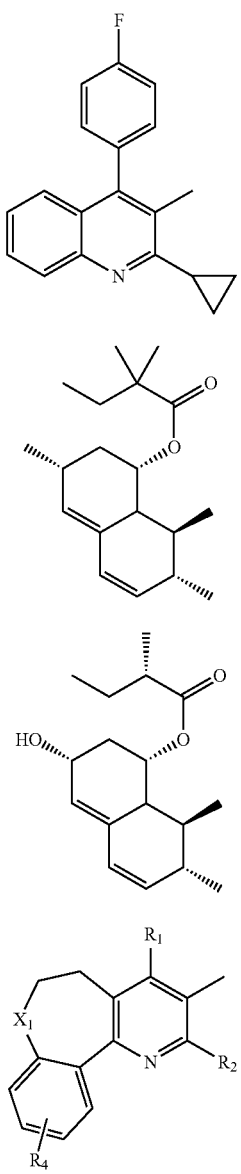

wherein $R_1$ and $R_2$ are same or different and are independently selected from alkyl, arylalkyl, cycloalkyl, alkenyl, cycloalkenyl, aryl, heteroaryl or cycloheteroalkyl, $R_4$ is H, halogen, $CF_3$, hydroxy, alkyl, alkoxy, alkanoylamino, aroylamino, or cyano, $X_1$ is $CH_2$, O, S or $NR_7$, wherein $R_7$ is H, alkyl, aryl, alkanoyl, aroyl, or alkoxycarbonyl, the process comprising:

(a) condensing a compound of Formula (1)

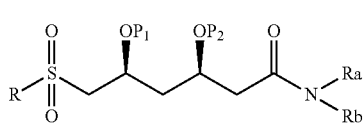

(1)

wherein $P_1$ and $P_2$ are alcohol protecting group or 1,3-diol protecting group and wherein R is

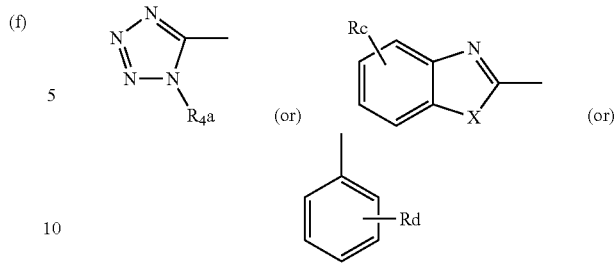

where $R_{4a}$ is alkyl, aryl, arylalkyl or cycloalkyl, Rc is H, alkyl, aryl, alkaoxy, haloalkyl, monohaloalkyloxy, dihaloalkyloxy, Rd is alkyl, aryl, arylalkyl, $CF_3$, halo or $NO_2$ and X is O, N—H, N-alkyl or S, Ra and Rb may be the same or different and each represents hydrogen, any of an alkyl group of 1 to 12 carbon atoms, an aryl group of 6 to 12 carbon atoms, an aralkyl group of 7 to 12 carbon atoms, with aldehyde compound

wherein $R_{10}$ is as defined as defined above, in presence of base such as sodium hydride, potassium tert-butoxide, LiHMDS or NaHMDS in an inert organic solvent to obtain compound of Formula (8);

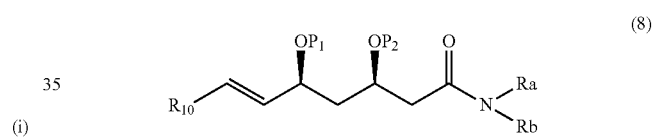

(8)

(b) hydrolyzing the compound of Formula (8) under acidic conditions to obtain compound of Formula (8A);

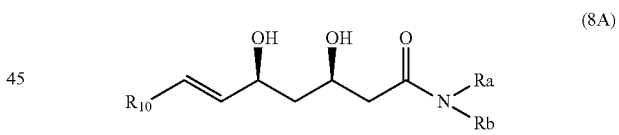

(8A)

(c) treating the compound of Formula (8A) with an alkali metal hydroxide to form corresponding alkali metal salt of Formula (9)

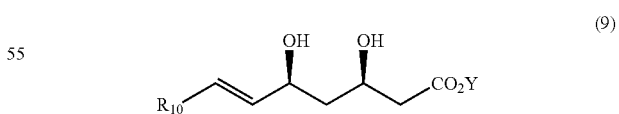

(9)

wherein, Y is $Na^+$, $K^+$, $Li^+$;

(d) optionally, treating alkali metal salt of HMG-CoA reductase inhibitors of Formula (9) with source of cation to obtain the HMG-CoA reductase inhibitors; and (e) isolating the HMG-CoA reductase inhibitors of Formula (9).

According the still further embodiments of the present invention, there is provided a process for the preparation of HMG-CoA reductase inhibitors of Formula (9)

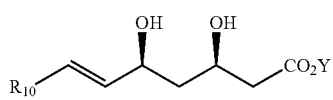  (9)

Y is Na$^+$, K$^+$, Li$^+$, Mg$^{2+}$, Ca$^{2+}$, Zn$^{2+}$, Ba$^{2+}$, Sr$^{2+}$; amine and R$_{10}$ is a hydrophobic anchor or residue of an HMG-CoA reductase inhibitor and can be selected from compounds of Formula (a) to (i)

(a)
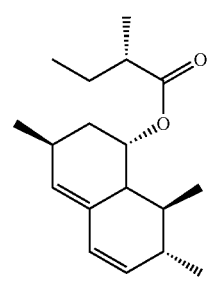

(b)
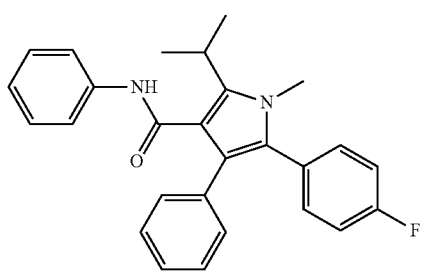

(c)
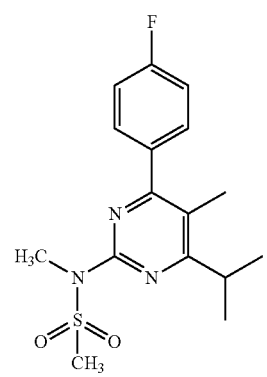 [SMILES: Cc1c(-c2ccc(F)cc2)nc(N(C)S(C)(=O)=O)nc1C(C)C]

(d)
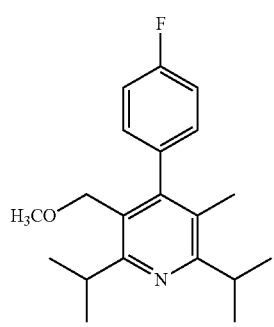

(e)
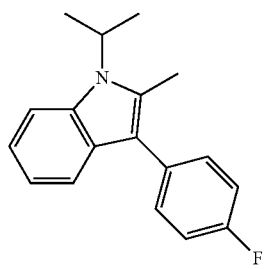

(f)
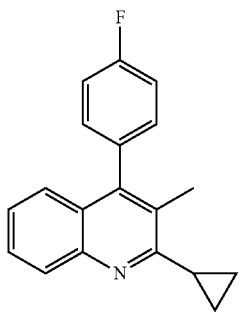

(g)
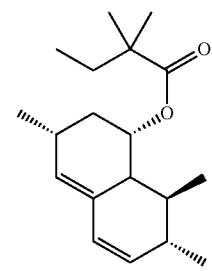

(h)
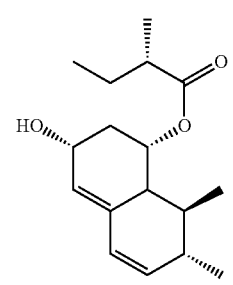

(i)
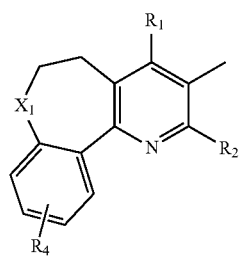

wherein R$_1$ and R$_2$ are same or different and are independently selected from alkyl, arylalkyl, cycloalkyl, alkenyl, cycloalkenyl, aryl, heteroaryl or cycloheteroalkyl; R$_4$ is H, halogen, CF$_3$, hydroxy, alkyl, alkoxy, alkanoylamino, aroylamino, or cyano; and X$_1$ is CH$_2$, O, S or NR$_7$, wherein R$_7$ is H, alkyl, aryl, alkanoyl, aroyl, or alkoxycarbonyl, the process comprising:

(a) condensing a compound of Formula (1B)

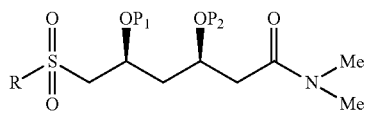
(1B)

wherein P$_1$ and P$_2$ are alcohol protecting group or 1,3-diol protecting group and wherein R is

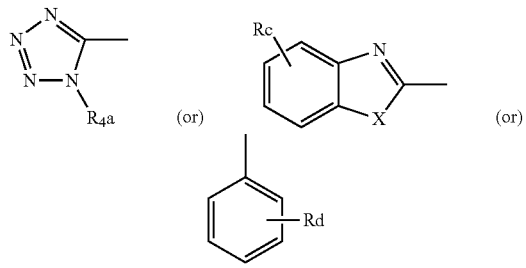

where R$_4$a is alkyl such as phenyl, aryl, arylalkyl or cycloalkyl,
Rc is H, alkyl, aryl, alkaoxy, haloalkyl, monohaloalkyloxy, dihaloalkyloxy,
Rd is alkyl, aryl, arylalkyl, CF$_3$, halo or NO$_2$ and X is O, N—H, N-alkyl or S,
Ra and Rb may be the same or different and each represents hydrogen, any of an alkyl group of 1 to 12 carbon atoms, an aryl group of 6 to 12 carbon atoms, an aralkyl group of 7 to 12 carbon atoms, with aldehyde compound

wherein R$_{10}$ is as defined as defined above, in presence of base such as sodium hydride, potassium tert-butoxide, LiHMDS or NaHMDS in an inert organic solvent to obtain compound of Formula (8B);

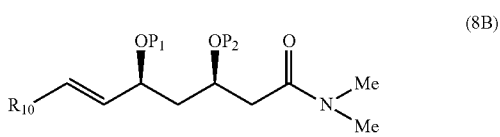
(8B)

(b) hydrolyzing the compound of Formula (8B) under acidic conditions to obtain compound of Formula (8A);

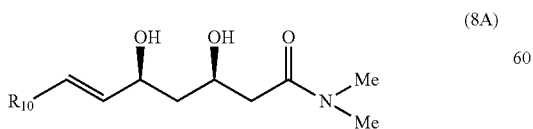
(8A)

(c) treating the compound of Formula (8A) with an alkali metal hydroxide to form corresponding alkali metal salt of Formula (9)

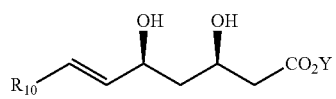
(9)

(d) optionally, treating alkali metal salt Formula (9) with source of cation; and
(e) isolating the HMG-CoA reductase inhibitors of Formula (9).

The sulfone compounds of general Formula (1) are useful intermediates in the preparation of dihydroxy acid HMG-CoA reductase inhibitors like pravastatin, atorvastatin, cerivastatin, fluvastatin, rosuvastatin, nisvastatin (pitavastatin), simvastatin, lovastatin and other dihydroxy acid or lactone thereof.

The aldehyde as shown above can be prepared as per the known process reported in the art, which is incorporated herein as the reference in its entirety.

According to the preferred embodiment, the present invention provides a process for the preparation of rosuvastatin calcium of Formula (9a)

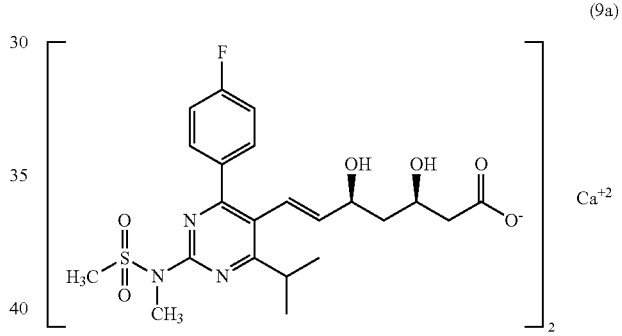
(9a)

the process comprising:
(a) condensing a compound of Formula (1a-B)

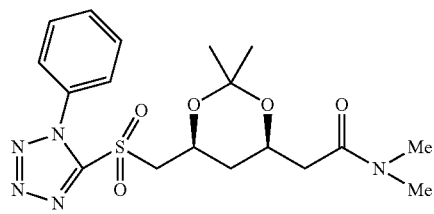
(1a-B)

with aldehyde compound of Formula

wherein $R_{10}$ is

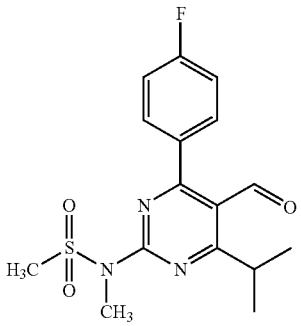 [SMILES: CC(C)c1nc(N(C)S(C)(=O)=O)nc(-c2ccc(F)cc2)c1C=O]

in presence of base such as sodium hydride, potassium tert-butoxide, LiHMDS or NaHMDS in a suitable organic solvent to obtain compound of Formula (8B2);

(8B2)

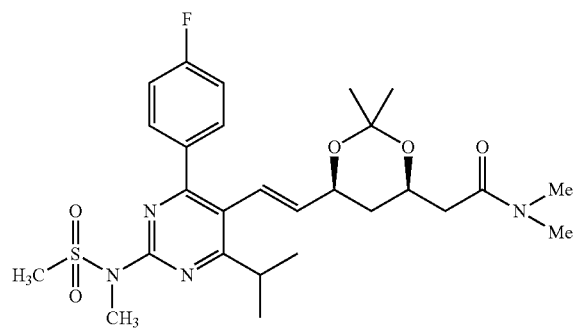

(b) hydrolyzing the compound of Formula (8B2) under acidic conditions to obtain compound of Formula (8B2-b);

(8B2-b)

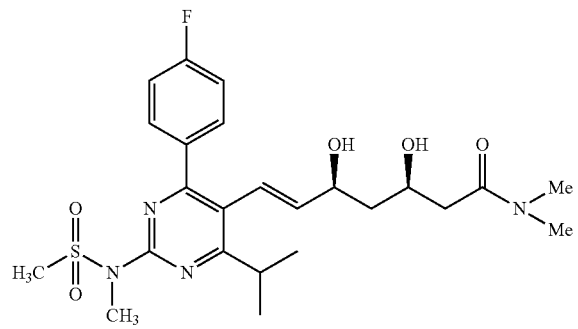

(c) treating the compound of Formula (8B2-b) with an alkali metal hydroxide to form corresponding alkali metal salt of Formula (9B);

(9B)

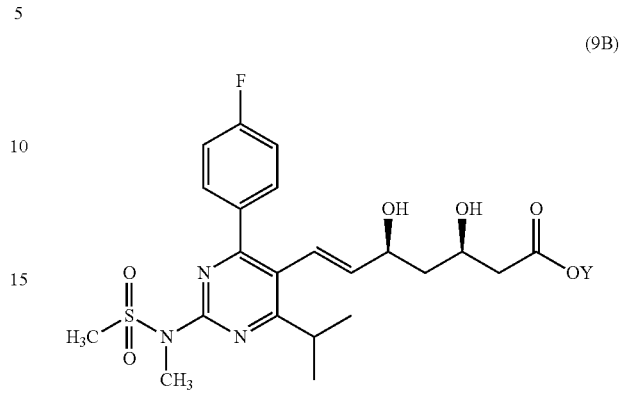

wherein, Y is $Na^+$, $K^+$, $Li^+$;

(d) treating alkali metal salt of rosuvastatin of Formula (9B) with source of calcium to obtain calcium salt of rosuvastatin; and (e) isolating the rosuvastatin calcium of Formula (9a).

In general, the process for the hydrolysis of compound (8B2) includes reacting compound (8B2) with an acid with one or more of hydrochloric acid, acetic acid, sulfuric acid, nitric acid, phosphoric acid and the like. The compound (8B2-b) is further treated with suitable alkali metal hydroxide comprises one or more of sodium hydroxide, potassium hydroxide, lithium hydroxide and the like to obtain compound (9B).

According to the preferred embodiment, the alkali metal salt of rosuvastatin is rosuvastatin potassium. In general, the further process includes treatment of rosuvastatin potassium with calcium sources selected from one or more of calcium chloride, calcium hydroxide, calcium acetate and hydrates thereof to obtain rosuvastatin calcium.

The rosuvastatin potassium salt obtained is further treated with mixture of toluene and ethyl acetate followed by treatment with suitable calcium source like calcium chloride, calcium acetate, calcium hydroxide and the like. In particular, calcium acetate is used to obtain rosuvastatin calcium salt. The isolated rosuvastatin calcium is in amorphous form.

It will be the scope of the present invention wherein the deprotecting the amide group of the product of Formula (8) can be hydrolyzed first with suitable base and then removal of 1,3-diol protecting group by treatment with acid with the provision both the hydrolysis sequence can be interchangeable to obtain compound of Formula (9), wherein $R_{10}$ is as defined above and Y is H or a pharmaceutically acceptable cation; and optionally followed by neutralization to give a compound of Formula (9) wherein Y is H, and/or optionally followed by conversion to another compound of Formula (9) wherein Y is calcium to obtain rosuvastatin calcium of Formula (9a).

The compound obtained after the removal of amide group from a compound of Formula (8B2-b) can be converted to amine salts of Formula (8-Amine Salt) for the purpose of purification. The amine salts may be directly isolated from the reaction mixture after the acid hydrolysis.

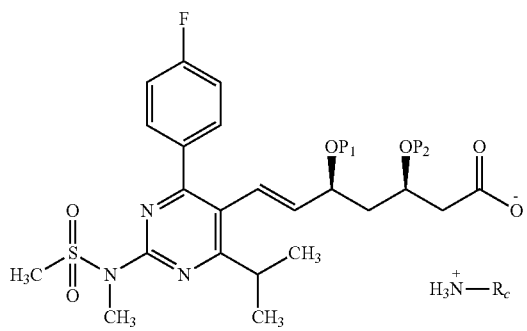

(8-Amine Salt)

wherein $R_c$ is $C_1$ to about $C_{10}$ alkyl, arylalkyl, alkanols, aryl etc.

Further process may include the salt breaking and deprotection of 1,3-diol protecting group and treatment with calcium acetate to obtain rosuvastatin calcium (9a).

According to the preferred embodiment, the present invention provides a novel intermediate compound 2-((4R,6S)-6-((E)-2-(4-(4-fluorophenyl)-6-isopropyl-2-(N-methylmethyl-sulfonamido)-pyrimidin-5-yl)vinyl)-2,2-dimethyl-1,3-dioxan-4-yl)-N,N-dimethylacetamide of Formula (8B2).

The novel compound (8B2) is characterized by an X-ray powder diffraction pattern having characteristics peaks expressed in degrees 2θ at 5.4°, 10.0°, 12.4°, 14.8°, 16.3°, 17.4°, 18.0°, 20.7°, 23.6°, 24.1°, 25.9°, and 27.2°±0.2°. Hence, compound (8B2) is having crystalline form.

The crystalline nature of compound (8B2) is further characterized by an IR spectrum having peaks at about 1633, 1543, 1508, 1442, 1384, 1232, 1197, 1161, 1082, 1026, 962, 848, 777, 567, and 511 cm$^{-1}$.

In an embodiment, the present invention also provides a process for the preparation of 2-((4R,6S)-6-(E)-2-(4-(4-fluorophenyl)-6-isopropyl-2-(N-methylmethylsulfonamido)pyrimidin-5-yl)vinyl)-2,2-dimethyl-1,3-dioxan-4-yl)-N,N-dimethylacetamide of Formula (8B2), (8B2)

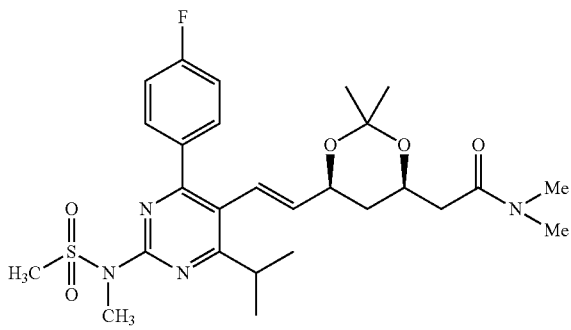

the process comprising:
(a) condensing a compound of Formula (1a-B)

(1a-B)

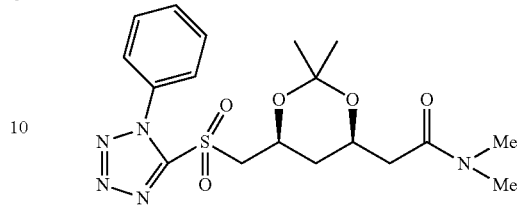

with aldehyde compound of Formula

$R_{10}$—CH wherein $R_{10}$ is

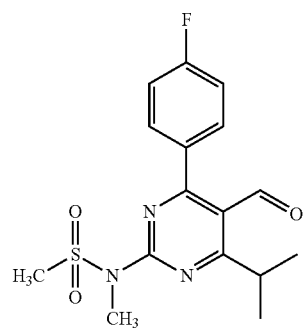

in presence of base such as sodium hydride, potassium tert-butoxide, LiHMDS or NaHMDS in a suitable organic solvent to obtain compound of Formula (8B2);
(b) extracting aqueous solution of compound of Formula (8B2) with water immiscible organic solvent;
(c) removing water immiscible organic solvent to obtain residue;
(d) treating the residue with suitable organic solvent;
(e) heating the reaction mixture at an elevated temperature;
(f) cooling the reaction mixture to ambient temperature; and
(g) isolating the 2-((4R,6S)-6-(E)-2-(4-(4-fluorophenyl)-6-isopropyl-2-(N-methylmethyl-sulfonamido)pyrimidin-5-yl)vinyl)-2,2-dimethyl-1,3-dioxan-4-yl)-N,N-dimethylacetamide in crystalline form.

The condensation of compound of formula (1) with aldehyde compound can be performed in suitable organic solvent selected from one or more of $C_1$-$C_4$ alcohol like methanol, ethanol, isopropanol, butanol and the like, $C_2$-$C_4$ ketone like acetone, methyl isobutyl ketone, amides like dimethyl formamide, dimethyl acetamide, N-methyl pyrrolidone, dimethylsulfoxide and the like to obtain novel compound of formula (8B2). The novel compound of (8B2) is extracted with water immiscible organic solvent selected from one or more of toluene, xylene, ethylbenzene, ethyl acetate, butyl acetate, methylene dichloride, and the like.

The aqueous layer is removed and the organic layer of water immiscible organic solvent is subjected to distillation to remove the solvent and obtain residue. The residue is further triturated with suitable organic solvent selected from one or more of C₁-C₄ alcohol like methanol, ethanol, isopropanol, butanol and the like, C₂-C₄ ketone like acetone, methyl isobutyl ketone, amides like dimethyl formamide, dimethyl acetamide, N-methyl pyrrolidone, dimethylsulfoxide, ethers like methyl tert-butyl ether, diisopropylether, cyclohexane, n-heptane, n-hexane and the like. In particular, the residue is triturated with methyl tert-butyl ether to obtain crystalline form of compound (8a-B).

In general, the residue is triturated with suitable organic solvent at an elevated temperature from about 40° C. to about 100° C. followed by cooling to an ambient temperature is from about 0° C. to about 30° C. to obtain crystalline form of compound (8B2).

In a most preferred embodiment, the present invention provides following novel compounds used as an intermediates for the preparation of HMG-CoA reductase inhibitors.
(S)-ethyl 3-hydroxy-4-(1-phenyl-1H-tetrazol-5-ylthio)butanoate (11a)
(S)-5-hydroxy-N,N-dimethyl-3-oxo-6-(1-phenyl-1H-tetrazol-5-ylthio)hexanamide (6a)
(3R,5S)-3,5-dihydroxy-N,N-dimethyl-6-(1-phenyl-1H-tetrazol-5-ylthio)hexanamide (5a)
2-((4R,6S)-2,2-diethyl-6-((1-phenyl-1H-tetrazol-5-ylthio)methyl)-1,3-dioxan-4-yl)-N,N-dimethylacetamide (2a-A)
2-((4R,6S)-2,2-dimethyl-6-((1-phenyl-1H-tetrazol-5-ylthio)methyl)-1,3-dioxan-4-yl)-N,N-dimethylacetamide (2a-B)
N,N-dimethyl-2-((2R,4S)-4-((1-phenyl-1H-tetrazol-5-ylthio)methyl)-1,5-dioxaspiro[5.5]undecan-2-yl)acetamide (2a-C)
2-((4R,6S)-2-ethyl-2-methyl-6-((1-phenyl-1H-tetrazol-5-ylthio)methyl)-1,3-dioxan-4-yl)-N,N-dimethylacetamide (2a-D)
2-((4R,6S)-2,2-diethyl-6-((1-phenyl-1H-tetrazol-5-ylsulfonyl)methyl)-1,3-dioxan-4-yl)-N,N-dimethylacetamide (1a-A)
2-((4R,6S)-2,2-dimethyl-6-((1-phenyl-1H-tetrazol-5-ylsulfonyl)methyl)-1,3-dioxan-4-yl)-N,N-dimethylacetamide (1a-B)
N,N-dimethyl-2-((2R,4S)-4-((1-phenyl-1H-tetrazol-5-ylsulfonyl)methyl)-1,5-dioxaspiro[5.5]undecan-2-yl)acetamide (1a-C)
2-((4R,6S)-2-ethyl-2-methyl-6-((1-phenyl-1H-tetrazol-5-ylsulfonyl)methyl)-1,3-dioxan-4-yl)-N,N-dimethylacetamide (1a-D)
2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)-N,N-dimethylacetamide (8B2)
2-((2R,4S)-4-((E)-2-(4-(4-fluorophenyl)-6-isopropyl-2-(N-methylmethylsulfonamido)pyrimidin-5-yl)vinyl)-1,5-dioxaspiro[5.5]undecan-2-yl)-N,N-dimethylacetamide (8B3)

As set forth in the following schemes, the process of the invention for the preparation of chiral diol sulfones and dihydroxy acid HMG CoA reductase inhibitors involves the following chemical reactions.

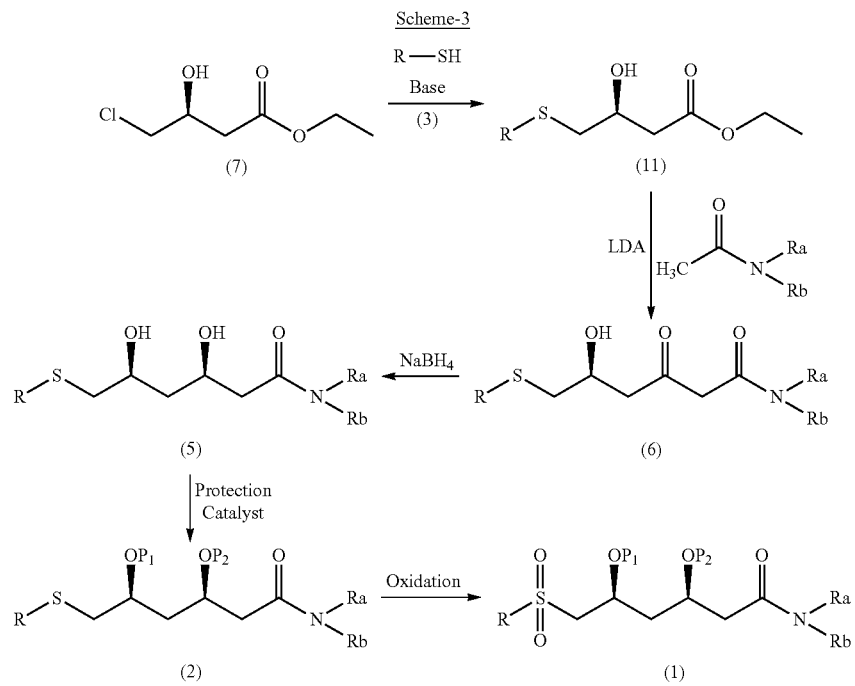

Scheme-3 wherein P₁ and P₂ are alcohol protecting group or 1,3-diol protecting group Ra and Rb may be the same or different and each represents hydrogen, any of an alkyl group of 1 to 12 carbon atoms, an aryl group of 6 to 12 carbon atoms, an aralkyl group of 7 to 12 carbon atoms.

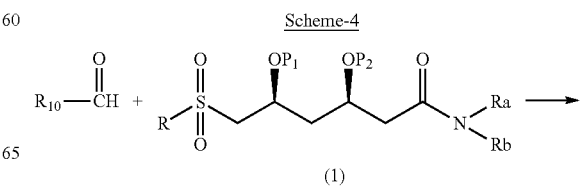

Scheme-4

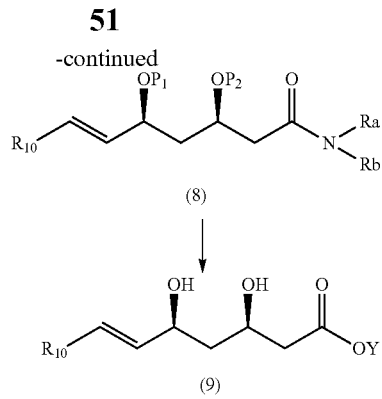

Having thus described the invention with reference to particular preferred embodiments and illustrative examples, those in the art would appreciate modifications to the invention as described and illustrated that do not depart from the spirit and scope of the invention as disclosed in the specification.

Example 1

Preparation of (S)-Ethyl-3-hydroxy-4-(1-phenyl-1H-tetrazol-5-ylthio)butanoate (11a)

121.2 g of triethylamine and 100 g of (S)-4-chloro-3-hydroxybutyric acid ester were added to the solution of 96.2 g of 1-phenyl-1H-terazole-5-thiol in 750 mL toluene at 25° C. The reaction mixture was heated to 80° C. to 85° C. for completion of reaction on TLC. The reaction mixture was cooled to 25° C. and treated with 200 mL of water and stirred to separate the layers. The separated aqueous layer was twice extracted with 100 mL toluene. The combined organic layer was treated with 300 mL HCl solution followed by washing with 200 ml water. The organic layer was distilled under vacuum below 50° C. The residue was treated with 200 ml hexane and stirred for 30 minutes. The solution was distilled under vacuum below 50° C. to remove hexane and obtain (S)-Ethyl-3-hydroxy-4-(1-phenyl-1H-tetrazol-5-ylthio)butanoate (11a) as an oil.

Example 2

Preparation of (S)-5-hydroxy-N,N-dimethyl-3-oxo-6-(1-phenyl-1H-tetrazol-5-ylthio)hexanamide (6a)

1000 mL THF and 132.27 g diisopropyl amine were taken in round bottom flask at 25° C. The reaction mixture was cooled to −10° C. and 531 mL of n-butyl amine was added to it. The reaction mixture was stirred for 30 minutes and further cooled to −40° C. 113 g N,N-dimethylacetamide solution in 1000 mL THF was gradually added to the reaction mixture and stirred for 2 hours. 100 g (S)-Ethyl-3-hydroxy-4-(1-phenyl-1H-tetrazol-5-ylthio)butanoate (11a) solution in 200 mL THF was added to the reaction mixture and stirred for 2 hours. After the completion of the reaction as monitored by TLC, the reaction mixture was quenched with 20% 1000 mL ammonium chloride solution at about −25° C. The separated aqueous layer was extracted with 400 mL ethyl acetate. The separated organic layer was washed with 1000 mL 1N HCl solution followed by washing with 1000 mL of water at 25° C. The organic layer was distilled under vacuum below 50° C. to obtain 100 g residue as an oil. The oily residue was taken in 400 mL hexane and distilled to obtain oil.

Example 3

Preparation of (3R,5S)-3,5-dihydroxy-N,N-dimethyl-6-(1-phenyl-1H-tetrazol-5-ylthio)hexanamide Formula (5a)

1000 mL THF and 28 g of diethoxymethylborane (DEMBO) were cooled to less than −60° C. in round bottom flask. 100 g oily residue solution of example-2 in 500 ml methanol was added and reaction mixture was stirred. 12.61 g sodium borohydride was added and stirred for 1 hour. After completion of the reaction as monitored by TLC, 33 mL acetic acid was slowly added and the reaction mixture was subjected to distillation under vacuum below 50° C. 500 mL methanol was added below 50° C. and heated to reflux at 65° C. to 70° C. Methanol was removed by distillation under vacuum and cooled to 28° C. to 35° C. 300 mL water and 100 mL methanol was added and the resulting reaction mixture was washed with 400 mL hexane at 25° C. The aqueous layer was treated with 400 mL methylene dichloride. The organic layer was washed with water and distilled under vacuum to remove methylene dichloride and obtain (3R,5S)-3,5-dihydroxy-N,N-dimethyl-6-(1-phenyl-1H-tetrazol-5-ylthio)hexanamide Formula (5a) as residue oil. The oily residue was taken in 100 mL hexane and distilled to obtain oil.

Example 4

Preparation of 2-((4R,6S)-2,2-dimethyl-6-(1-phenyl-1H-tetrazol-5-ylthio)methyl)-1,3-dioxan-4-yl)-N,N-dimethylacetamide of Formula (2a-B)

100 g chiral sulfide diol of example-3 and 200 mL acetone were taken in round bottom flask at 25° C. 100 g 2,2-dimethoxypropane was added and cooled below 20° C. 2 mL methane sulphonic acid was added and the reaction mixture was heated at 30° C. for 12 hours. After the completion of the reaction as monitored by TLC, the reaction mixture was quenched with sodium bicarbonate solution followed by washing with 500 mL hexane. The separated aqueous layer was extracted with toluene followed by distillation under vacuum below 50° C. to remove toluene to obtain chiral diol sulfide (2a-B).

Example 5

Preparation of N,N-dimethyl-2-((2R,4S)-4-((1-phenyl-1H-tetrazol-5-ylsulfonyl)methyl)-1,5-dioxaspiro[5.5]undecan-2-yl)acetamide of Formula (1a-B) (chiral sulfone diol)

100 g of chiral sulfide diol of Formula (2a-B) and 500 mL IPA were taken in round bottom flask at 25° C. 5.0 g of ammonium heptamolybdate tetrahydrate was added followed by addition of 78.6 g of hydrogen peroxide solution in 78.6 mL water. After completion of reaction on TLC, the resulting mass was quenched with 1000 mL of water. 500 mL methylene dichloride was added and stirred for 30 minutes. The separated organic layer was treated with 100 mL of 10% sodium thio sulfate solution.

The further separated organic layer was dried over sodium sulfate and distilled under atmospheric pressure to obtain chiral sulfone diol (1a-B) as an oil.

Example 6

Preparation of Chiral Diol Sulfone Derivatives as Per Process of Example-5

25 g chiral sulfide (2a-B) and 100 mL methanol were taken in round bottom flask at room temperature. The reaction mixture was stirred and treated with 1.25 g of ammonium heptamolybdate tetrahydrate at 0° C.-5° C. followed by addition of 50% 20.3 g hydrogen peroxide at 0° C.-5° C. The reaction mixture was stirred overnight at room temperature and again cooled to 0° C. to 5° C. The product thus obtain was filtered and washed with 25 mL chilled methanol to obtain 11.2 g chiral diol sulfones of Formula (1a-B).

The above process can be repeated by using chiral sulfide of Formula (2a-A), (2a-B'), (2a-C) etc for preparing the chiral sulfoxides of Formula (1a-A), (1a-B'), (1a-C) etc, respectively by replacing the chiral sulfide of Formula (2a-B).

Example 7

Preparation of Compound of Formula (8B2)

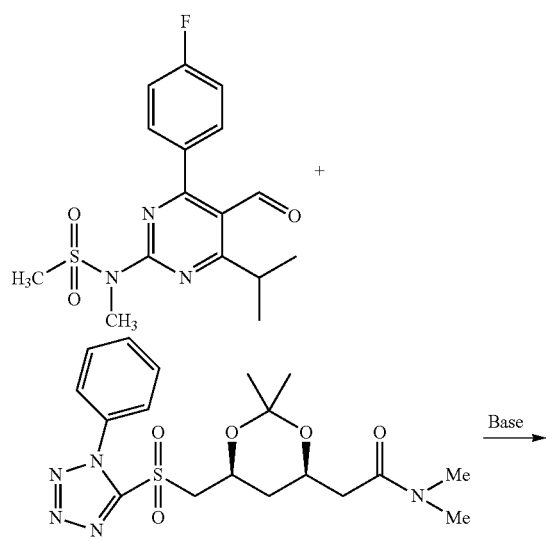

(1a-B)

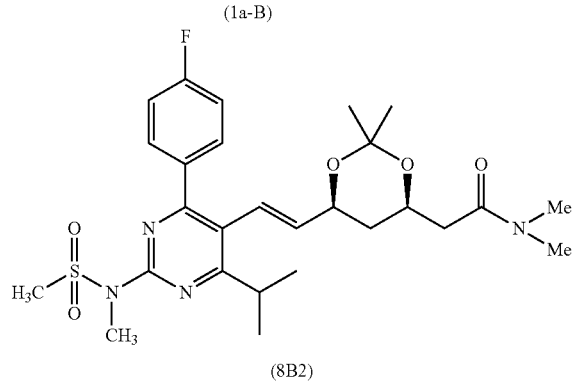

(8B2)

2.5 g aldehyde compound, 3.6 g chiral diol sulfone (1a-B) and 50 mL THF were taken in round bottom flask at 35° C. under nitrogen atmosphere. The reaction mixture was cooled to −70° C. to −78° C. and treated with 10 g of NaH. The reaction mixture was stirred for 7-8 hours and quenched with ammonium chloride after completion of the reaction as monitored by TLC. The layers were separated at room temperature followed by washing organic layer with saturated sodium 38 mL saturated sodium bicarbonate solution. The organic layer was distilled under vacuum below 50° C. The solid residue 7.1 g was treated with 35 mL methanol and heated at 55° C. for 1 hour, cooled back to 0° C. and stirred for 1 hour. The isolated product was filtered and washed with chilled methanol to obtain 2.8 g compound of Formula (8B2).

The above process can be repeated by using chiral diol sulfone of Formula (1a-A), (1a-C), (1a-D) for preparing the compound of Formula (8B1), (8B3) and (8B4) respectively by replacing the compound of Formula (1a-B).

Example-8

Preparation of Ethylamine Salt of Compound (8B2 Amine Salt)

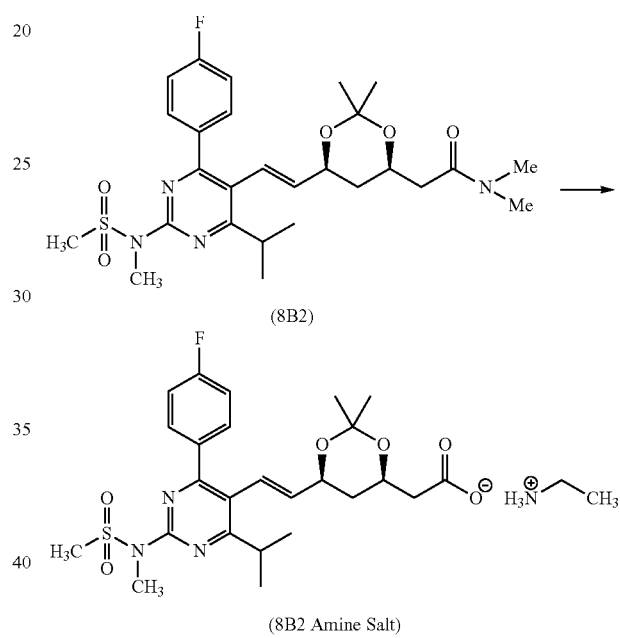

(8B2)

(8B2 Amine Salt)

2.5 g of compound of Formula (8B2) and 50 mL methylene dichloride was distilled atmospherically at 40° C. to 50° C. The reaction mixture was treated with 21 mL 10% sodium hydroxide solution and 100 mL methanol. The methylene dichloride was removed azeotropically at 45° C. to 50° C. After MDC removal, the reaction mixture was treated with 200 mL methanol and temperature was raised upto reflux for about 60° C. to 65° C. for 6-8 hours. After the completion of the reaction on TLC, methanol was distilled under vacuum at 40° C. to 45° C.

Further, the reaction mixture was treated with 20 mL of water and 50 mL of acetonitrile and cooled to 0° C. to 10° C. The pH of the reaction mixture was adjusted using dilute HCl at 0° C. to 10° C. The organic layer was separated and treated with ethylamine gas to adjust the pH to about 8 to 9 at 0° C. to 10° C. The reaction mixture was maintained at about 25° C. to 35° C. for 1 hour. The product thus obtained was filtered and washed with chilled with acetonitrile. The solid was dried at 50° C. to 55° C. to obtain ethyl amine salt of compound of Formula (8B2-Amine Salt).

The process disclosed in Example-11 can be repeated in the similar manner by replacing ethylamine with n-propylamine, tert-butyl amine or other suitable organic amine to obtain amine salt of compound of Formula (8B2-Amine Salt)

Example-9

Preparation of Amorphous Rosuvastatin Calcium

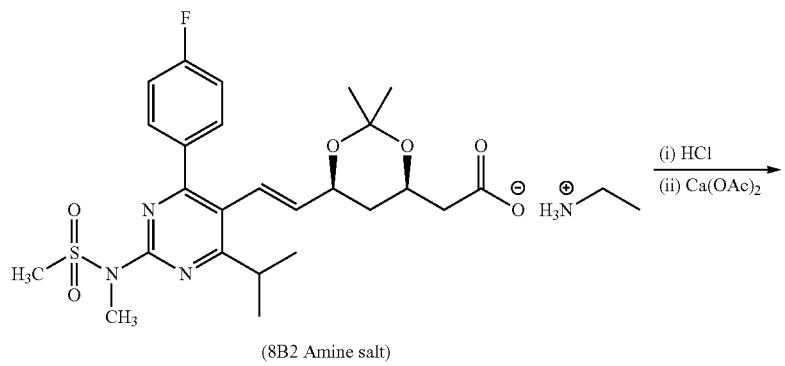

(8B2 Amine salt)

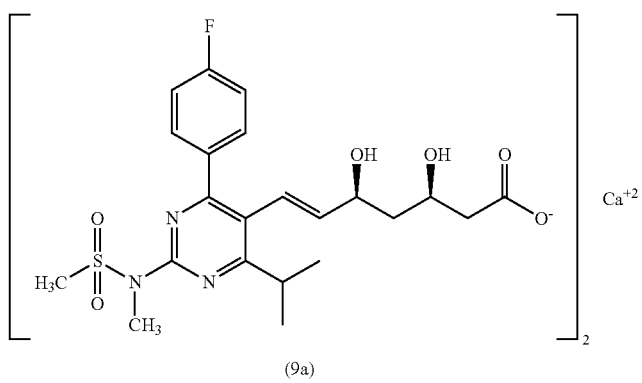

(9a)

10 g of ethylamine salt of Formula (8B2 Amine salt) and 90 mL acetonitrile in RBF at 25° C. to 35° C. The reaction mixture was cooled to 0° C. to 10° C. The reaction mixture was stirred and treated with 25 mL 1N HCl and maintained for 2 hours at 20° C. to 25° C. After the completion of the reaction on TLC, the reaction mixture was treated with 10% potassium hydroxide solution at 10° C. to 15° C. and maintained for 2 hours at 20° C. to 25° C. After completion of the reaction as monitored by TLC, the reaction mixture was treated with 1N HCl to get pH of 8 to 8.5 and charcoalized. The reaction mixture was filtered and washed with acetonitrile. The filtrate was extracted with mixture of toluene and ethyl acetate in the ratio of 7:3. at 25° C. to 35° C. The solvents were distilled under vacuum at 35° C. to 40° C. to remove the traces of solvents and further treated with water to make up the volume upto 80 mL. The aqueous solution was treated with 3.2 g of calcium acetate solution in 15 mL of water and maintained for 1 hour at 20° C. to 30° C. The solid thus obtained was filtered and washed with water. The solid was dried at 40° C. under vacuum for 10 to 12 hours to obtain amorphous rosuvastatin calcium. Purity by HPLC >99.0%.

Example-10

Preparation of Rosuvastatin Calcium of (9a)

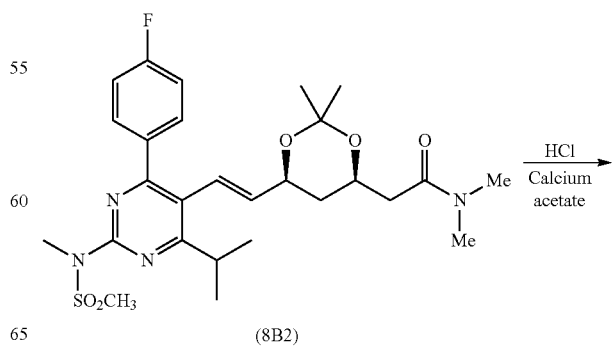

(8B2)

-continued

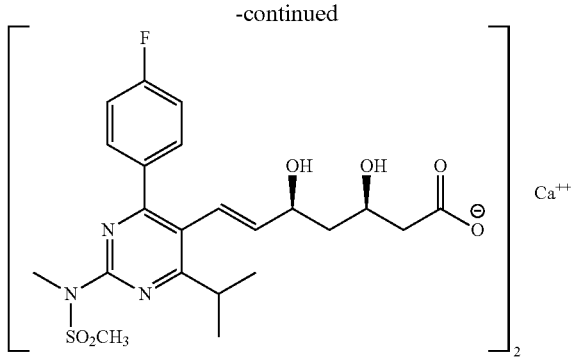

100 g of compound (8B2) and 2500 mL methanol were taken at 15° C. in a reaction vessel and treated with aqueous HCl. The reaction mixture was stirred for 2 hours and 118.6 g (10%) potassium hydroxide solution was added. The reaction mixture was stirred for 70 hours at 35° C. till the completion of the reaction by TLC. The reaction mixture was cooled and treated with aqueous HCl. The reaction mixture was charcoalized and filtered. The filtrate was distilled and treated with 500 mL mixture of toluene and ethyl acetate in ratio of 1:1. The aqueous layer was separated and washed with mixture of toluene and ethyl acetate. The aqueous layer was distilled below 45° C. and cooled. The residue was treated with acetic acid followed by extraction with 1000 mL methylene dichloride. The methylene dichloride layer was washed with water and distilled. The residue was treated with 200 mL methanol to get clear solution upon stirring. The reaction mixture was treated with 7 g KOH solution in 500 mL water and stirred. The reaction mixture was distilled to remove methanol under vacuum and treated with aqueous HCl. The reaction mixture was charcoalized and filtered. The filtrate was treated with 29 g calcium acetate solution in 300 mL water at 35° C. The product was precipitated upon stirring for 1 hour. The product was filtered and washed with water to obtain rosuvastatin calcium.

Purification:

The rosuvastatin calcium wet-cake obtained above and 300 mL water were heated at about 45° C. for 1 hour and cooled to 30° C. to obtain rosuvastatin calcium. The product was filtered and dried under vacuum at 40° C. to 45° C. to obtain amorphous rosuvastatin calcium.

While the invention has been described in terms of its specific embodiments, certain modifications and equivalents will be apparent to those skilled in the art and are intended to be included within the scope of the invention.

ADVANTAGES OF THE INVENTION

1) The present invention provides an improved process for the synthesis of chiral diol sulfones of general Formula (1).
2) The present invention provides an improved process for preparing HMG-CoA reductase inhibitors using chiral diol sulfones of general Formula (1).
3) The present invention provides an improved process for preparing rosuvastatin calcium via chiral diol sulfone of Formula (1).
4) The present invention provides novel intermediates like compound of Formula (1), (2), (5'), (6'), (8), and (11) useful for the preparation of Rosuvastatin Calcium.
5) The present invention provides the processes for the preparation of novel chiral diol sulfones (1) and intermediates thereof.
6) The present invention provides the processes for the preparation of key intermediates for synthesis of rosuvastatin calcium via novel chiral diol sulfones (1).
7) The process is simple, safe, cost effective and can be employed for commercial production.

We claim:

1. A compound of Formula (1),

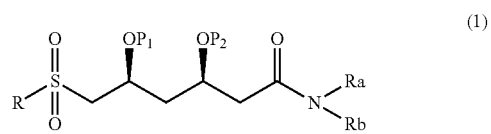

wherein $P_1$ and $P_2$ are alcohol protecting groups or 1,3-diol protecting group, R is selected from:

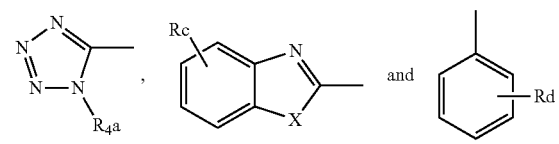

wherein $R_4a$ is selected from alkyl, aryl, arylalkyl and cycloalkyl,

Rc is selected from H, alkyl, aryl, alkaoxy, haloalkyl, monohaloalkyloxy, and dihaloalkyloxy, Rd is selected from alkyl, aryl, arylalkyl, $CF_3$, halo and $NO_2$ and X is selected from O, N—H, N-alkyl and S, Ra and Rb are same or different and each represents hydrogen, an alkyl group of 1 to 12 carbon atoms, an aryl group of 6 to 12 carbon atoms, or an aralkyl group of 7 to 12 carbon atoms.

2. The compound as claimed in claim 1, selected from:

(a)

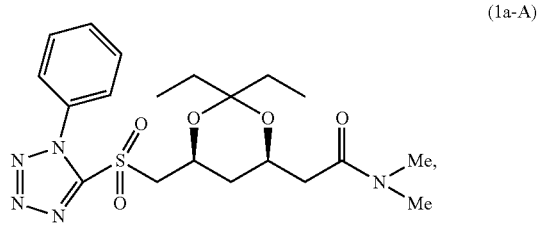

(b)

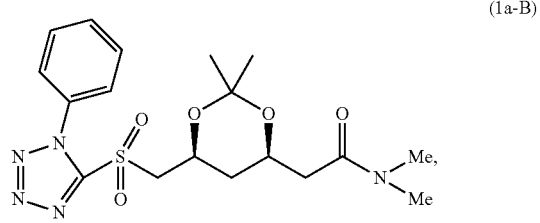

-continued (c)

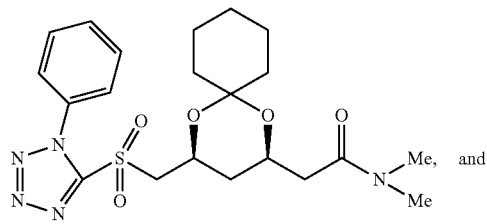
(1a-C)

(d)

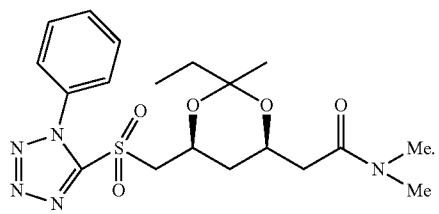
(1a-D)

3. A compound of Formula (2),

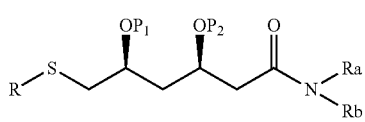
(2)

wherein $P_1$ and $P_2$ are alcohol protecting groups or 1,3-diol protecting group;
R is selected from:

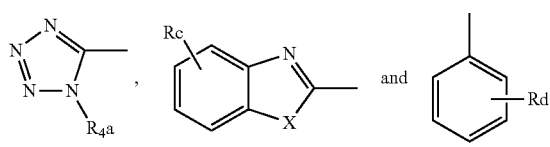

wherein $R_4a$ is selected from alkyl, aryl, arylalkyl and cycloalkyl,
Rc is selected from H, alkyl, aryl, alkaoxy, haloalkyl, monohaloalkyloxy, and dihaloalkyloxy,
Rd is selected from alkyl, aryl, arylalkyl, $CF_3$, halo and $NO_2$ and X is selected from O, N—H, N-alkyl and S,
Ra and Rb are same or different and each represents hydrogen, an alkyl group of 1 to 12 carbon atoms, an aryl group of 6 to 12 carbon atoms, or an aralkyl group of 7 to 12 carbon atoms.

4. The compound as claimed in claim 3, selected from:

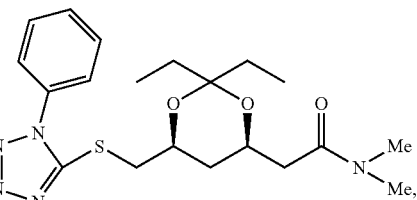
(2a-A)

(a)

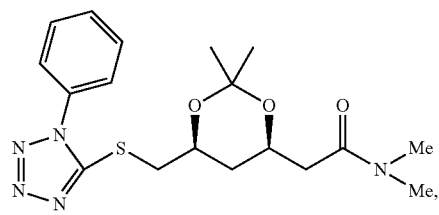
(2a-B)

(b)

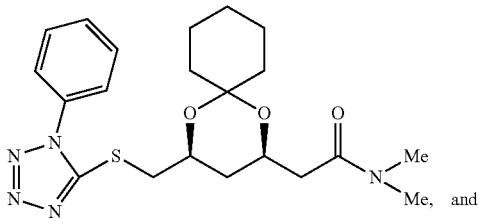
(2a-C)

(c)

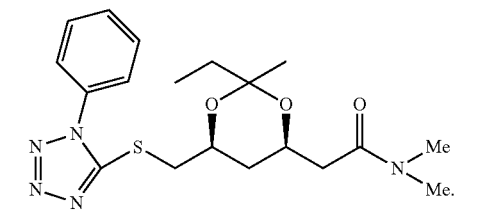
(2a-D)

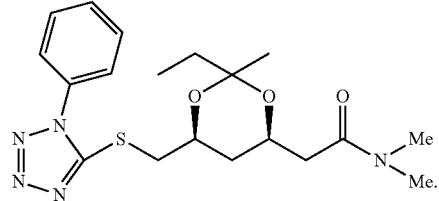
(d)

5. A compound of Formula (5),

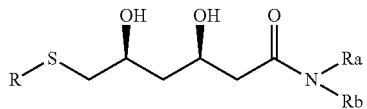
(5)

wherein R is selected from:

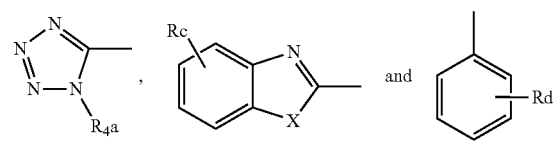

wherein $R_4a$ is selected from alkyl, aryl, arylalkyl and cycloalkyl,

Rc is selected from H, alkyl, aryl, alkaoxy, haloalkyl, monohaloalkyloxy, and dihaloalkyloxy, Rd is selected from alkyl, aryl, arylalkyl, $CF_3$, halo and $NO_2$ and X is selected from O, N—H, N-alkyl and S, Ra and Rb are same or different and each represents hydrogen, an alkyl group of 1 to 12 carbon atoms, an aryl group of 6 to 12 carbon atoms, or an aralkyl group of 7 to 12 carbon atoms.

6. The compound of Formula (5) as claimed in claim 5, which is represented by:

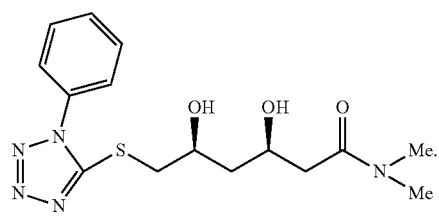

(5a)

7. A compound of Formula (6),

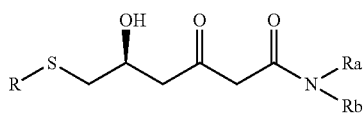

(6)

wherein R is selected from:

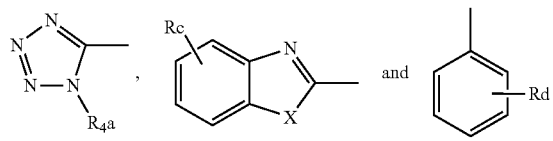

wherein $R_4a$ is selected from alkyl, aryl, arylalkyl and cycloalkyl,

Rc is selected from H, alkyl, aryl, alkaoxy, haloalkyl, monohaloalkyloxy, and dihaloalkyloxy, Rd is selected from alkyl, aryl, arylalkyl, $CF_3$, halo and $NO_2$ and X is selected from O, N—H, N-alkyl and S, Ra and Rb are same or different and each represents hydrogen, an alkyl group of 1 to 12 carbon atoms, an aryl group of 6 to 12 carbon atoms, or an aralkyl group of 7 to 12 carbon atoms.

8. A process for the preparation of a compound of Formula (1),

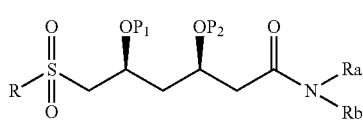

(1)

as claimed in claim 1, the process comprising the steps of:
(a) reacting (S)-4-chloro-3-hydroxybutyric acid ester (7),

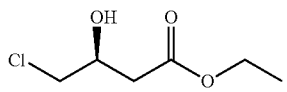

(7)

with a thiol derivative of Formula 3, selected from

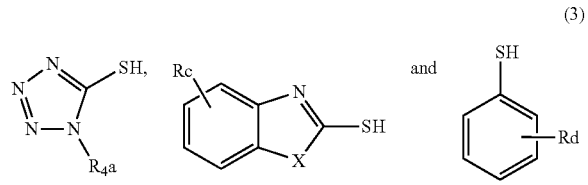

(3)

wherein $R_4a$, Rc, Rd and X are as defined in claim 1, in a suitable organic solvent in the presence of a base to obtain a compound of Formula (11);

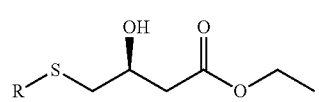

(11)

(b) reacting the compound of Formula (11) with a compound of Formula (7a),

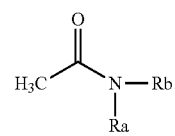

(7a)

wherein Ra and Rb are the same or different and each represents hydrogen, an alkyl group of 1 to 12 carbon atoms, an aryl group of 6 to 12 carbon atoms, or an aralkyl group of 7 to 12 carbon atoms, in an inert organic solvent to obtain a compound of Formula (6);

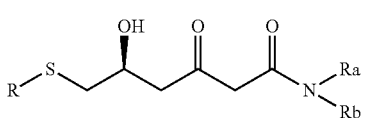

(6)

(c) treating the compound of Formula (6) with dialkylalkoxyborane in the presence of a base to obtain a compound of Formula (5);

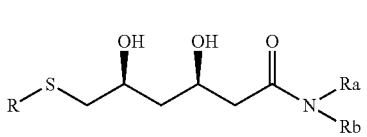

(5)

(d) reacting the compound of Formula (5) with a suitable reagent in the presence of a catalyst in a polar organic solvent to obtain a compound of Formula (2),

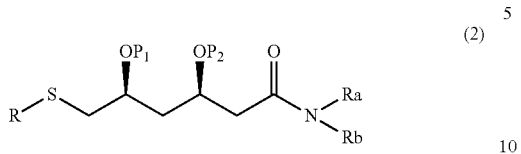
(2)

wherein R, $P_1$, $P_2$, Ra and Rb are as defined in claim 1; and
(e) oxidizing the compound of Formula 2 with a suitable oxidizing agent to obtain the compound of Formula 1.

9. The process as claimed in step (a) of claim 8, wherein the suitable organic solvent comprises one or more of toluene, xylene, ethylbenzene, cyclohexane, hexane, heptane, methylene dichloride, ethylene dichloride, and ethyl acetate.

10. The process as claimed in step (a) of claim 8, wherein the base comprises one or more inorganic bases selected from the group consisting of sodium hydroxide, potassium hydroxide, sodium bicarbonate, potassium bicarbonate, and sodium hydride, or one or more organic bases selected from the group consisting of triethylamine, diisopropylethylamine, diisopropyl amine, 1,8-diazabicycloundec-7-ene (DBU), and pyridine.

11. The process as claimed in step (c) of claim 8, wherein the dialkylalkoxyborane is selected from group consisting of diethylmethoxyborane, diethylethoxyborane, and dimethylethoxyborane.

12. The process as claimed in step (c) of claim 8, wherein the base comprises one or more of alkali metal hydrides selected from the group consisting of sodium hydride, potassium hydride, lithium hydride, sodium borohydride, potassium borohydride, and lithium aluminium hydride.

13. The process as claimed in step (c) of claim 8, further comprising purifying the compound of Formula (5') in a suitable organic solvent selected from the group consisting of one or more of $C_1$-$C_4$ alcohol, water, and aliphatic hydrocarbons.

14. The process as claimed in step (d) of claim 8, wherein the suitable reagent comprises one or more of 2,2-dimethoxypropane, 2,2-dimethoxypentane, 1,1-dimethoxycyclohexane, and 2,2-dimethoxybutane.

15. The process as claimed in step (d) of claim 8, wherein the catalyst comprises one or more of camphor sulfonic acid, methane sulphonic acid, ethane sulfonic acid, pyridinium p-toluene sulfonic acid, and p-toluene sulfonic acid.

16. The process as claimed in step (e) of claim 8, wherein the suitable oxidizing agent comprises one or more of hydrogen peroxide, m-chloroperbenzoic acid, sodium hypochloride, N-chlorosuccimide, N-bromosuccinmide, and oxone.

17. A process for the preparation of a compound of Formula 8,

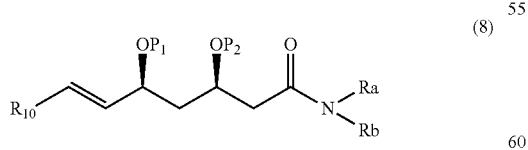
(8)

wherein $P_1$ and $P_2$ are alcohol protecting groups or 1,3-diol protecting group;
Ra and Rb may be same or different and each represents, an alkyl group of 1 to 12 carbon atoms, an aryl group of 6 to 12 carbon atoms, or an aralkyl group of 7 to 12 carbon atoms;

$R_{10}$ is a hydrophobic anchor or a residue of an HMG-CoA reductase inhibitor and can be selected from compounds of Formula (a) to (i),

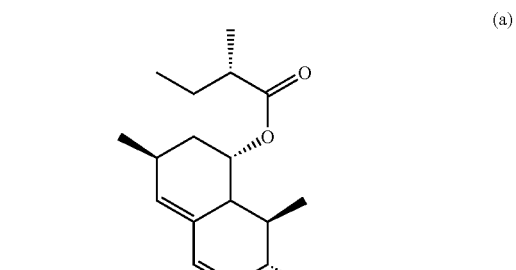
(a)

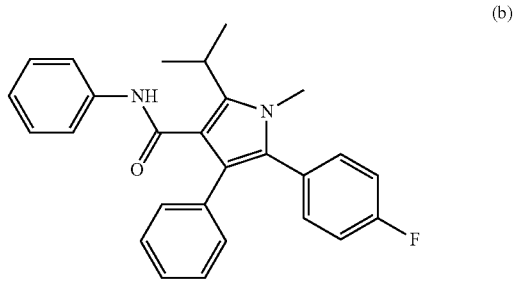
(b)

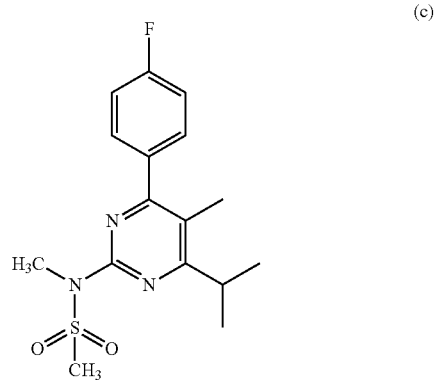
(c)

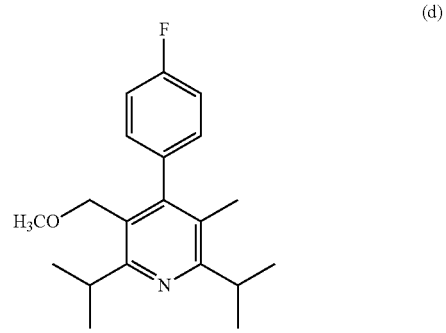
(d)

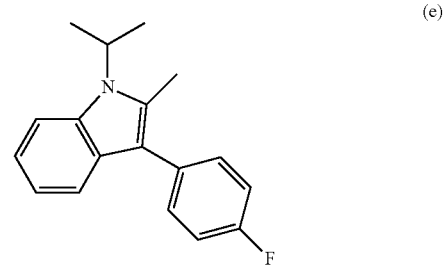
(e)

-continued (f)
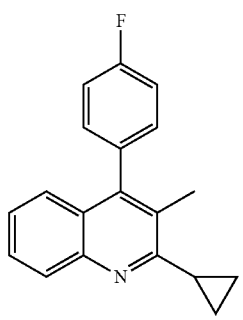

(g)
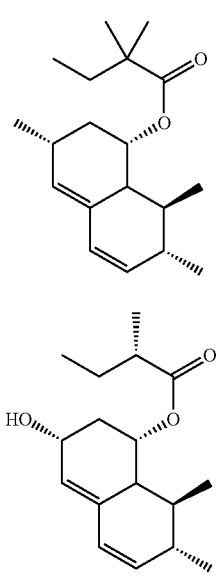

(h)

(i)
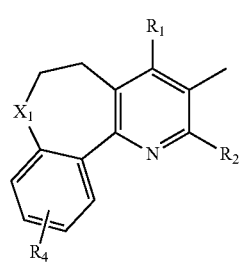

wherein $R_1$ and $R_2$ are same or different and are independently selected from alkyl, arylalkyl, cycloalkyl, alkenyl, cycloalkenyl, aryl, heteroaryl or cycloheteroalkyl; $R_4$ is H, halogen, $CF_3$, hydroxy, alkyl, alkoxy, alkanoylamino, aroylamino, or cyano; and $X_1$ is $CH_2$, O, S or $NR_7$, wherein $R_7$ is H, alkyl, aryl, alkanoyl, aroyl, or alkoxycarbonyl, the process comprising the steps of: condensing a compound of Formula (1), (1)
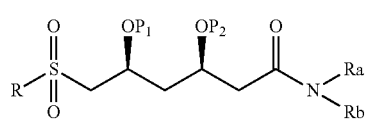

with an aldehyde compound of Formula,

wherein $R_{10}$ is as defined above, in the presence of a base selected from sodium hydride, potassium tert-butoxide, LiHMDS and NaHMDS in an inert organic solvent to obtain the compound of Formula (8).

18. A process for the preparation of a compound of Formula (8B2), (8B2)
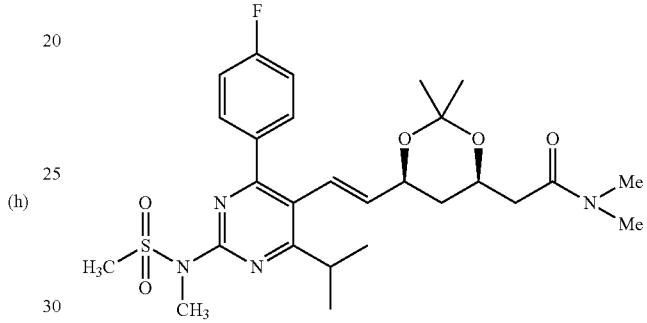

the process comprising the steps of:
(a) reacting chiral sulfide diol of Formula (5a), (5a)
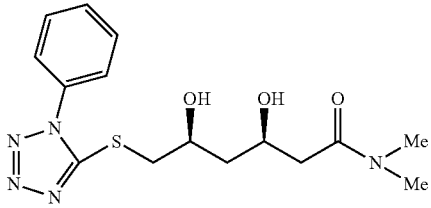

with 2,2-dimethoxypropane to obtain a compound of Formula (2a-B);

(2a-B)
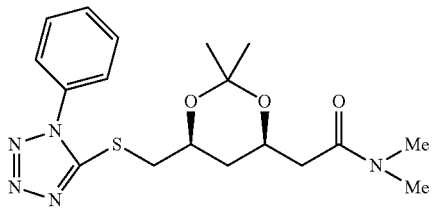

(b) oxidizing the compound of formula (2a-B) with a suitable oxidizing agent to provide a compound of the Formula (1a-B);

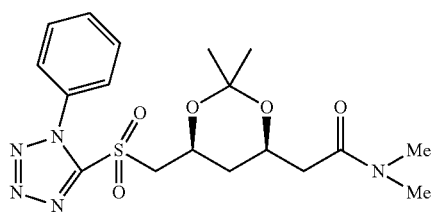
(1a-B)

(c) condensing the compound of Formula (1a-B) with an aldehyde compound of Formula,

wherein $R_{10}$ is, a hydrophobic anchor or a residue of an HMG-CoA reductase inhibitor and is selected from a compound of Formula

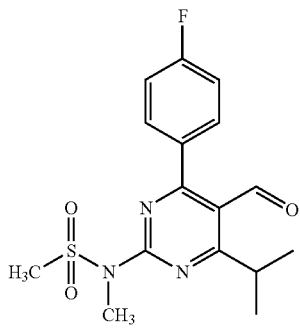 [SMILES: CC(C)c1nc(N(C)S(C)(=O)=O)nc(-c2ccc(F)cc2)c1C=O]

in the presence of a base selected from the group consisting of sodium hydride, potassium tert-butoxide, LiHMDS and NaHMDS in a suitable organic solvent to obtain the compound of Formula (8B2).

19. The process as claimed in claim 18, wherein the reaction of step (a) is performed in the presence of a catalyst selected from one or more of camphor sulfonic acid, methane sulphonic acid, ethane sulfonic acid, pyridinium p-toluene sulfonic acid, p-toluene and sulfonic acid.

20. The process as claimed in claim 18, wherein the suitable oxidizing agent comprises one or more of hydrogen peroxide, m-chloroperbenzoic acid, sodium hypochloride, N-chlorosuccimide, N-bromosuccinmide, and oxone.

21. The process as claimed in claim 17, wherein the suitable organic solvent comprises one or more of $C_1$-$C_4$ alcohol selected from methanol, ethanol, isopropanol, and butanol; $C_2$-$C_4$ ketone selected from acetone, methyl and isobutyl ketone; amides selected from dimethylformamide, dimethylacetamide, N-methylpyrrolidone, and dimethylsulfoxide.

22. A process for the preparation of an HMG-CoA reductase inhibitor of Formula (9),

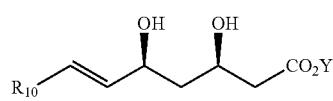
(9)

wherein

Y is selected from the group consisting of $Na^+$, $K^+$, $Li^+$, $Mg^{2+}$, $Ca^{2+}$, $Zn^{2+}$, $Ba^{2+}$, $Sr^{2+}$; and amine and $R_{10}$ is a hydrophobic anchor or residue of an HMG-CoA reductase inhibitor and is selected from a compound of Formula (a) to (i),

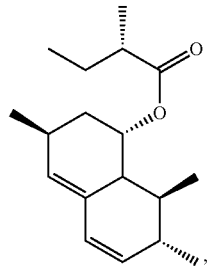
(a)

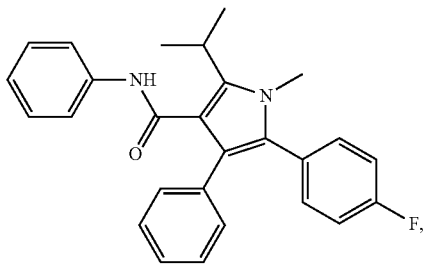
(b)

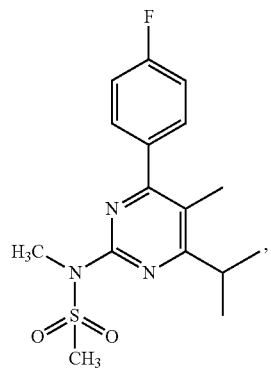
(c)

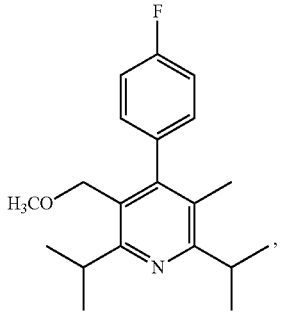
(d)

-continued (e)
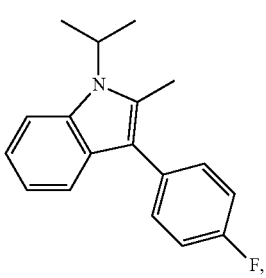

(f)
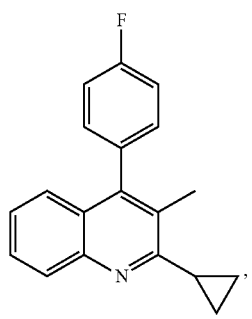

(g)
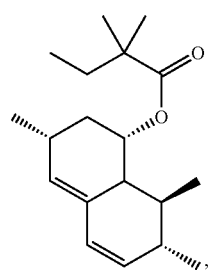

(h)
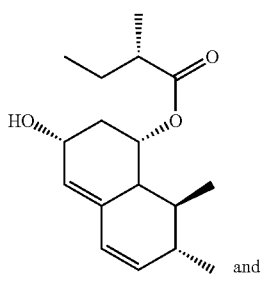
and (i)
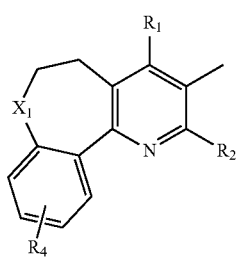

wherein $R_1$ and $R_2$ are the same or different and are independently selected from alkyl, arylalkyl, cycloalkyl, alkenyl, cycloalkenyl, aryl, heteroaryl and cycloheteroalkyl; $R_4$ is selected from H, halogen, $CF_3$, hydroxy, alkyl, alkoxy, alkanoylamino, aroylamino, and cyano; $X_1$ is selected from $CH_2$, O, S and $NR_7$, wherein $R_7$ is selected from H, alkyl, aryl, alkanoyl, aroyl, and alkoxycarbonyl, the process comprising:

(a) condensing a compound of Formula (1)

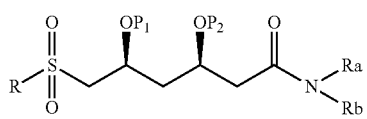
(1)

wherein $P_1$ and $P_2$ are alcohol protecting groups or 1,3-diol protecting group;
R is selected from:

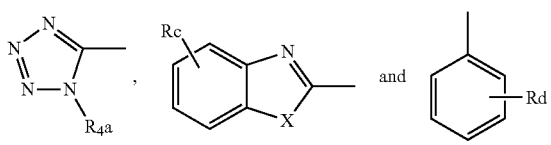
and wherein $R_4a$ is selected from alkyl, aryl, arylalkyl and cycloalkyl,
Rc is selected from H, alkyl, aryl, alkaoxy, haloalkyl, monohaloalkyloxy, and dihaloalkyloxy,
Rd is selected from alkyl, aryl, arylalkyl, $CF_3$, halo and $NO_2$ and X is selected from O, N—H, N-alkyl and S,
Ra and Rb are same or different and each represents an alkyl group of 1 to 12 carbon atoms, an aryl group of 6 to 12 carbon atoms, or an aralkyl group of 7 to 12 carbon atoms, with an aldehyde compound,

wherein $R_{10}$ is as defined above, in the presence of a base selected from sodium hydride, potassium tert-butoxide, LiHMDS and NaHMDS in an inert organic solvent to obtain a compound of Formula (8);

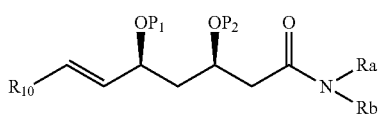
(8)

(b) hydrolyzing the compound of Formula (8) under acidic conditions to obtain a compound of Formula (8A);

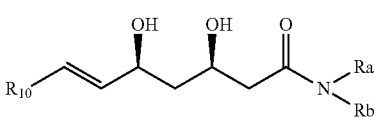
(8A)

(c) treating the compound of Formula (8A) with an alkali metal hydroxide to form the corresponding alkali metal salt of Formula (9),
(d) optionally treating the alkali metal salt of Formula (9) with a source of cation; and
(e) isolating the HMG-CoA reductase inhibitors of Formula (9).

23. A process for the preparation of an HMG-CoA reductase inhibitor of general Formula (9),
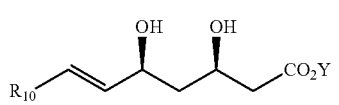
(9)
wherein
Y is selected from the group consisting of $Na^+$, $K^+$, $Li^+$, $Mg^{2+}$, $Ca^{2+}$, $Zn^{2+}$, $Ba^{2+}$, $Sr^{2+}$; and amine and
$R_{10}$ is a hydrophobic anchor or residue of an HMG-CoA reductase inhibitor and is selected from a compound of Formula (a) to (i),
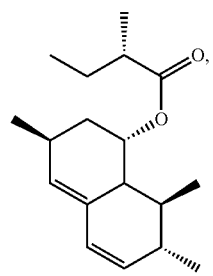
(a)
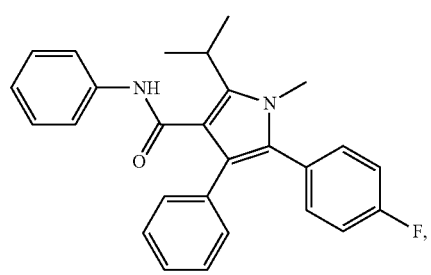
(b)
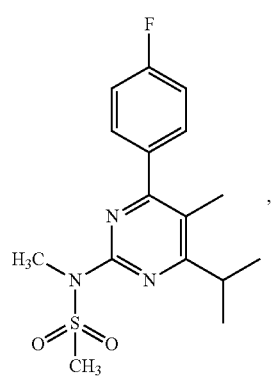
(c)
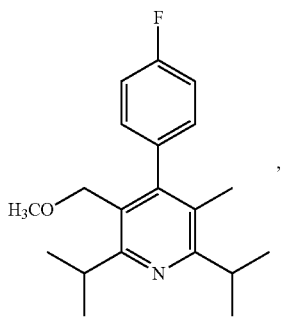
(d)
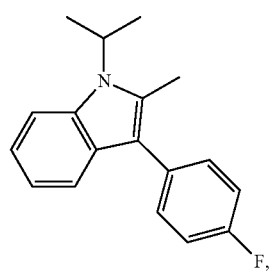
(e)
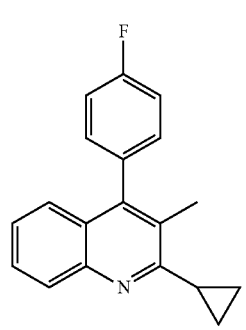
(f)
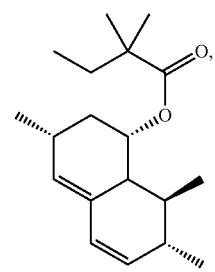
(g)
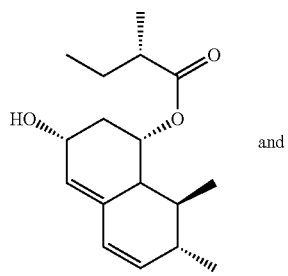
and (h)

-continued

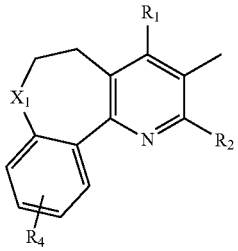
(i)

wherein R₁ and R₂ are the same or different and are independently selected from alkyl, arylalkyl, cycloalkyl, alkenyl, cycloalkenyl, aryl, heteroaryl and cycloheteroalkyl; R₄ is selected from H, halogen, CF₃, hydroxy, alkyl, alkoxy, alkanoylamino, aroylamino, and cyano; X₁ is selected from CH₂, O, S and NR₇, wherein R₇ is selected from H, alkyl, aryl, alkanoyl, aroyl, and alkoxycarbonyl, the process comprising:

(a) condensing a compound of Formula (1B)

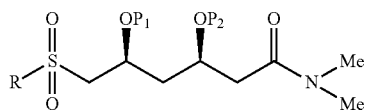
(1B)

wherein P₁ and P₂ are alcohol protecting groups or 1,3-diol protecting group;

R is selected from:

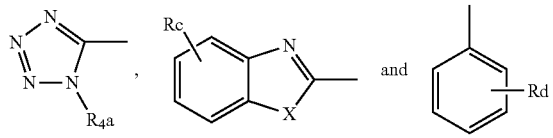

wherein R₄a is selected from alkyl, aryl, arylalkyl and cycloalkyl,

Rc is selected from H, alkyl, aryl, alkaoxy, haloalkyl, monohaloalkyloxy, and dihaloalkyloxy, Rd is selected from alkyl, aryl, arylalkyl, CF₃, halo and NO₂ and X is selected from O, N—H, N-alkyl and S, Ra and Rb are same or different and each represents an alkyl group of 1 to 12 carbon atoms, an aryl group of 6 to 12 carbon atoms, or an aralkyl group of 7 to 12 carbon atoms, with an aldehyde compound,

wherein R₁₀ is as defined above, in the presence of a base selected from sodium hydride, potassium tert-butoxide, LiHMDS and NaHMDS in an inert organic solvent to obtain a compound of Formula (8B);

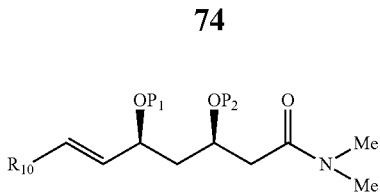
(8B)

(b) hydrolyzing the compound of Formula (8B) under acidic conditions to obtain a compound of Formula (8A);

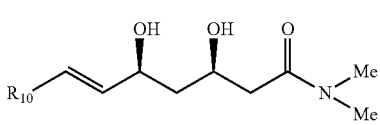
(8A)

(c) treating the compound of Formula (8A) with an alkali metal hydroxide to form the corresponding alkali metal salt of Formula (9), (d) optionally treating the alkali metal salt of Formula (9) with a source of cation; and (e) isolating the HMG-CoA reductase inhibitor of Formula (9).

24. A process for the preparation of rosuvastatin calcium of Formula (9a),

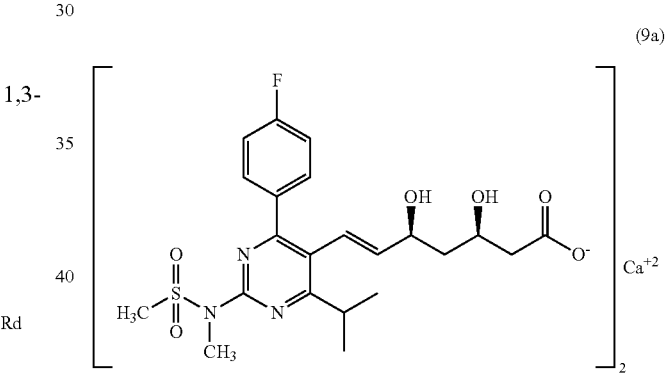
(9a)

the process comprising:

(a) condensing a compound of Formula (1 a-B),

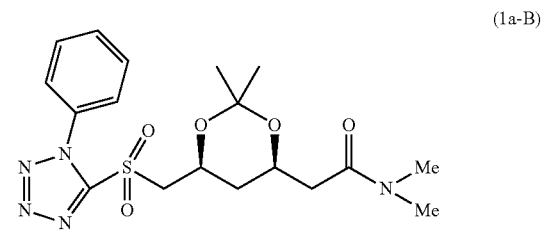 [SMILES: CN(C)C(=O)C[C@H]1C[C@@H](CS(=O)(=O)c2nnnn2-c2ccccc2)OC(C)(C)O1]
(1a-B)

with an aldehyde compound of Formula,

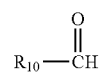

wherein R₁₀ is

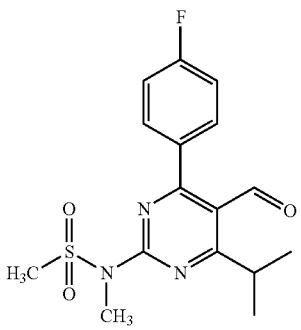 [SMILES: CC(C)c1nc(N(C)S(C)(=O)=O)nc(-c2ccc(F)cc2)c1C=O]

in the presence of a base selected from sodium hydride, potassium tert-butoxide, LiHMDS and NaHMDS in a suitable organic solvent to obtain a compound of Formula (8B2);

(8B2)

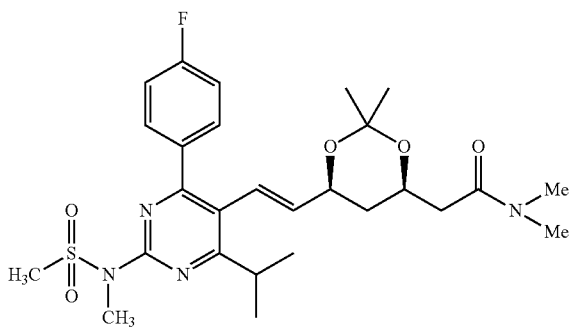

(b) hydrolyzing the compound of Formula (8B2) under acidic conditions to obtain a compound of Formula (8B2-b);

(8B2-b)

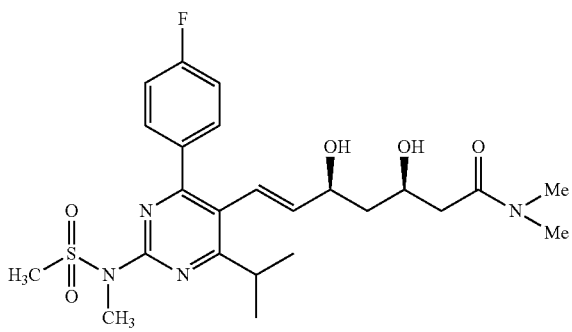

(c) treating the compound of Formula (8B2-b) with an alkali metal hydroxide to form the corresponding alkali metal salt of Formula (9B);

(9B)

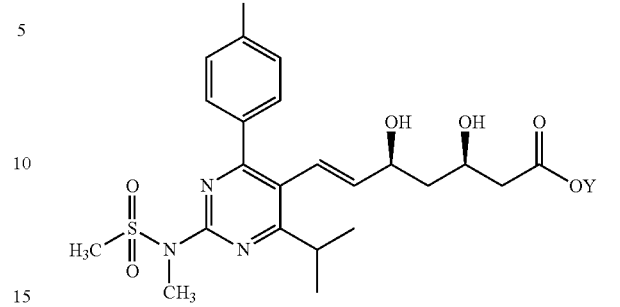

wherein, Y is selected from Na⁺, K⁺, and Li⁺;

(d) treating the alkali metal salt of rosuvastatin of Formula (9) with a source of calcium to obtain a calcium salt of rosuvastatin; and (e) isolating the rosuvastatin calcium of Formula (9a).

25. The process as claimed in claim 24, wherein the hydrolysis of compound (8B2) under acidic conditions can be done by one or more of hydrochloric acid, acetic acid, sulfuric acid, nitric acid, phosphoric acid, and the like.

26. The process as claimed in claim 24, wherein the alkali metal hydroxide is selected from one or more of sodium hydroxide, potassium hydroxide, and lithium hydroxide.

27. The process as claimed in claim 24, wherein the alkali metal salt of rosuvastatin is rosuvastatin potassium.

28. The process as claimed in claim 24, wherein the calcium source is selected from one or more of calcium chloride, calcium hydroxide, calcium acetate and hydrates thereof.

29. The process as claimed in claim 24, wherein the rosuvastatin calcium is isolated in amorphous form.

30. A process for the preparation of 2-(4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)-N,N-dimethylacetamide of Formula (8B2), (8B2)

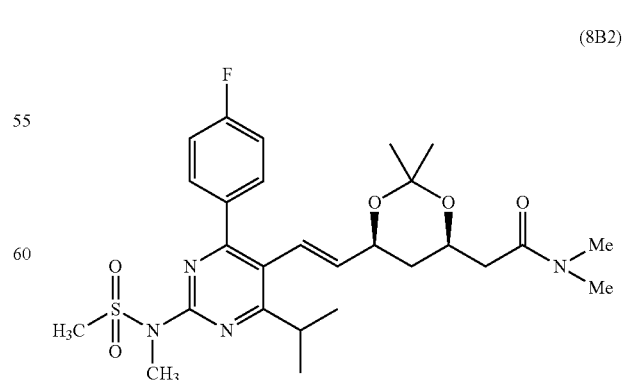

the process comprising the steps of:

(a) condensing a compound of Formula (1a-B),

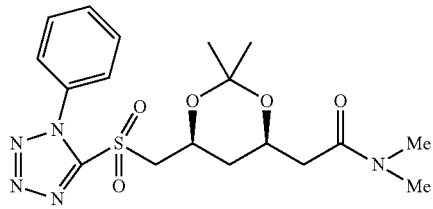

(1a-B)

with an aldehyde compound of Formula,

wherein $R_{10}$ is

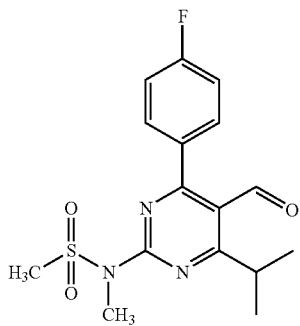 [SMILES: CC(C)c1nc(N(C)S(C)(=O)=O)nc(-c2ccc(F)cc2)c1C=O]

in the presence of a base selected from sodium hydride, potassium tert-butoxide, LiHMDS and NaHMDS in a suitable organic solvent to obtain a compound of Formula (8B2);

(b) extracting the compound of Formula (8B2) with a water immiscible organic solvent;

(c) removing the water immiscible organic solvent to obtain a residue;

(d) treating the residue with a suitable organic solvent;

(e) heating reaction mixture of step (d) at an elevated temperature;

(f) cooling the reaction mixture to ambient temperature; and (g) isolating 2-((4R,6S)-6-((E)-2-(4-(4-fluorophenyl)-6-isopropyl-2-(N-methylmethyl-sulfonamido)pyrimidin-5-yl)vinyl)-2,2-dimethyl-1,3-dioxan-4-yl)-N,N-dimethylacetamide in crystalline form.

31. The process as claimed in claim 30, wherein in step (a) the suitable organic solvent comprises one or more of $C_1$-$C_4$ alcohol selected from methanol, ethanol, isopropanol, and butanol, $C_2$-$C_4$ ketone selected from acetone, methyl and isobutyl ketone, and amides selected from dimethylformamide, dimethylacetamide, N-methylpyrrolidone, and dimethylsulfoxide.

32. The process as claimed in claim 30, wherein the water immiscible organic solvent comprises one or more of toluene, xylene, ethylbenzene, ethyl acetate, butyl acetate, and methylene dichloride.

33. The process as claimed in claim 30, wherein in step (d) the suitable organic solvent comprises one or more of $C_1$-$C_4$ alcohol selected from methanol, ethanol, isopropanol, and butanol and, $C_2$-$C_4$ ketone selected from acetone and methyl isobutyl ketone, amides selected from dimethylformamide, dimethylacetamide, N-methylpyrrolidone, and dimethylsulfoxide, and ethers selected from methyl tert-butyl ether, diisopropylether, cyclohexane, n-heptane, and n-hexane.

34. The process as claimed in claim 30, wherein the elevated temperature is from about 40° C. to about 100° C.

35. The process as claimed in claim 30, wherein the ambient temperature is from about 0° C. to about 30° C.

36. The process as claimed in step (c) of claim 13, wherein the aliphatic hydrocarbon is selected from n-hexane, n-heptane, cyclohexane, methylene dichloride and toluene.

* * * * *